(12) United States Patent
Chae et al.

(10) Patent No.: US 7,341,991 B2
(45) Date of Patent: Mar. 11, 2008

(54) INHIBITORS OF AMYLOID PRECURSOR PROTEIN PROCESSING

(75) Inventors: Chi-Bom Chae, Pohang (KR); Yong Song Gho, Pohang (KR); Chan Hyun Na, Pohang (KR); Sanghee Jeon, Pohang (KR)

(73) Assignees: Posco, Pohang (KR); Postech Foundation, Pohang (KR)

( * ) Notice: Subject to any disclaimer, the term of this patent is extended or adjusted under 35 U.S.C. 154(b) by 0 days.

(21) Appl. No.: 11/467,123

(22) Filed: Aug. 24, 2006

(65) Prior Publication Data

US 2007/0027089 A1  Feb. 1, 2007

Related U.S. Application Data

(63) Continuation-in-part of application No. 11/027,859, filed on Dec. 30, 2004, now abandoned.

(51) Int. Cl.
*A61K 38/00* (2006.01)
(52) U.S. Cl. ......................................................... 514/2
(58) Field of Classification Search ...................... None
See application file for complete search history.

(56) References Cited

U.S. PATENT DOCUMENTS 6,329,163 B1   12/2001   Anderson et al.
6,713,276 B2 *  3/2004   Cordell et al. ................ 435/23

FOREIGN PATENT DOCUMENTS

WO    WO 98/07850        8/1997
WO    WO 02/36614 A2    11/2001

OTHER PUBLICATIONS

Yamada, "Cerebral amyloid angiopathy: An overview", Neuropathology (2000), 20(1): 8-22.
Citron et al., "Mutation of the beta-amyloid precursor protein in familial Alzheimer's disease increases beta-protein production", Nature (1992), 360: 672-674.
Schenk et al., "Immunization with amyloid-beta attenuates Alzheimer-disease-like pathology in the PDAPP mouse", Nature (1999), 400(6740): 173-177.
Lewis et al., "Enhanced Neurofibrillary Degeneration in Transgenic Mice Expressing Mutant Tau and APP", Science (2001), 293(5534): 1487-1491.
Calhoun et al., "Neuron loss in APP transgenic mice", Nature (1998), 395(6704): 755-756.
Vassar et al., "A-Beta-Generating Enzymes: Recent Advances in Beta- and Gamma-Secretase Research", Neuron (2000), 27(3): 419-422.
Yankner, "Mechanisms of Neuronal Degeneration in Alzheimer's Disease", Neuron (1996), 16(5): 921-932.
Haass et al., "Amyloid beta-peptide is produced by cultured cells during normal metabolism", Nature (1992), 359: 322-325.
Seubert et al., Secretion of beta-amyloid precursor protein cleaved at the amino terminus of the beta-amyloid peptide, Nature (1993), 361: 260-263.
Sisodia, "Beta-Amyloid precursor protein cleavage by a membrane-bound protease", Proc. Natl. Acad. Sci. USA (1992), 89: 6075-6079.
Forman et al., "Differential Effects of the Swedish Mutant Amyloid Precursor Protein on Beta-Amyloid Accumulation and Secretion in Neurons and Nonneuronal Cells", J. Biol. Chem. (1997), 272: 32247-32253.
Chyung et al., "Novel Beta-Secretase Cleavage of Beta-Amyloid Precursor Protein in the Endoplasmic Reticulum/Intermediate Compartment of NT2N Cells", J. Cell. Bio. (1997), 138: 671-680.
Goate et al., "Segregation of a missense mutation in the amyloid precursor protein gene with familial Alzheimer's disease", Nature (1991), 349: 704-706.
Giaccone et al., "Down patients: extracellular preamyloid deposits precede neuritic degeneration and senile plaques", Neuroscience Letters (1989), 97: 232-238.
Jarrett et al., "The Carboxy Terminus of the Beta Amyloid Protein Is Critical for the Seeding of Amyloid Formation: Implications for the Pathogenesis of Alzheimer's Disease", Biochemistry (1993), 32: 4693-7.
Seubert et al., "Isolation and quantification of soluble Alzheimer's beta-peptide from biological fluids", Nature (1992), 359: 325-327.
Thomas et al., "Beta-Amyloid-mediated vasoactivity and vascular endothelial damage", Nature (1996), 380 (6570): 168-171.
Sommer, "Alzheimer's disease and the amyloid cascade hypothesis: ten years on", Curr. Opin. Pharmacol. (2002), 2(1): 87-92.
Marti et al., "Systemic hypoxia changes the organ-specific distribution of vascular endothelial growth factor and its receptors", Proc. Natl. Acad. Sci. USA (1998), 95(26): 15809-15814.
Hardy et al., "Alzheimer's Disease: The Amyloid Cascade Hypothesis", Science (1992), 256(5054): 184-185.
Hsiao et al., "Correlative Memory Deficits, A-BetaElevation, and Amyloid Plaques in Transgenic Mice", Science (1996), 274(5284): 99-102.
Sisodia et al., "Evidence That Beta-Amyloid Protein in Alzheimer's Disease Is Not Derived by Normal Processing", Science (1990), 248: 492-495.
Iwatsubo et al., "Visualization of A-Beta42(43) and A-Beta40 in Senile Plaques with End-Specific A-Beta Monoclonals: Evidence That an Initially Deposited Species Is A-Beta42(43)", Neuron (1993), 13: 45-53.
Jarrett et al., "Seeding "One-Dimensional Crystallization" of Amyloid: A Pathogenic Mechanism in Alzheimer's Disease and Scrapie?", Cell (1993), 73: 1055-1058.

(Continued)

*Primary Examiner*—Cecilia J. Tsang
*Assistant Examiner*—Maury Audet
(74) *Attorney, Agent, or Firm*—JHK Law; Joseph Hyosuk Kim

(57) ABSTRACT

Disclosed is a method of using a compound as an inhibitor for β-secretase, wherein the compound is capable of binding to the site within the β-secretase recognition and/or cleavage site on amyloid precursor protein to specifically inhibit the β-secretase's activity to cleave amyloid precursor protein with maintaining its activities to other substrates. Further, the present invention relates to inhibitors of amyloid precursor protein (APP) processing which bind to the site within the β-secretase or γ-secretase cleavage and/or recognition site on amyloid precursor protein.

2 Claims, 37 Drawing Sheets

OTHER PUBLICATIONS

Gho et al., "Anti-angiogenin Activity of the Peptides Complementary to the Receptor-binding Site of Angiogenin", The Journal of Biological Chemistry (1997), 272(39): 24294-24299.

Grüninger-Leitch et al., "Substrate and Inhibitor Profile of BACE (B-Secretase) and Comparison with Other Mammalian Aspartic Proteases", The Journal of Biological Chemistry (2002), 277(7): 4687-4693.

Murphy et al., "y-Secretase, Evidence for Multiple Proteolytic Activities and Influence of Membrane Positioning of Substrate on Generation of Amyloid B Peptides of Varying Length", The Journal of Biological Chemistry (1999), 274(17): 11914-11923.

Beher et al., "Generation of C-terminally truncated amyloid-B peptides is dependent on y-secretase activity", Journal of Neurochemistry (2002), 82: 563-575.

Shearman et al., "L-685,458 as Aspartyl Protease Transition State Mimic, Is a Potent Inhibitor of Amyloid B-Protein Precursor y-Secretase Activity", Biochemistry (2000), 39: 8698-8704.

* cited by examiner

| | | |
|---|---|---|
| | c-Sub M | S E F C I Q I H F R |
| N-terminal deletion | c-Sub M ΔN1 | E F C I Q I H F R |
| | c-Sub M ΔN2 | F C I Q I H F R |
| | c-Sub M ΔN3 | C I Q I H F R |
| | c-Sub M ΔN4 | I Q I H F R |
| | c-Sub M ΔN5 | Q I H F R |
| C-terminal deletion | c-Sub M ΔC1 | S E F C I Q I H F |
| | c-Sub M ΔC2 | S E F C I Q I H |
| | c-Sub M ΔC3 | S E F C I Q I |
| | c-Sub M ΔC4 | S E F C I Q |
| | c-Sub M ΔC5 | S E F C I |
| | c-Sub M ΔC6 | S E F C |
| | c-Sub M ΔC7 | S E F |

Peptide synthesis

| | |
|---|---|
| c-Sub M ΔC1N3 | CI QIHF |
| c-Sub M ΔC1N3.A1 | A——— |
| c-Sub M ΔC1N3.A2 | —A—— |
| c-Sub M ΔC1N3.A3 | ——A—— |
| c-Sub M ΔC1N3.A4 | ———A—— |
| c-Sub M ΔC1N3.A5 | ———A— |
| c-Sub M ΔC1N3.A6 | ————A |

A

| peptide | BACE activity(%) | % inhibition |
|---|---|---|
| c-Sub M ΔC1N3 | 0.0 | 100.00000 |
| c-Sub M ΔC1N3.A1 | 66.9 | -2.90769 |
| c-Sub M ΔC1N3.A2 | 42.9 | 34.06154 |
| c-Sub M ΔC1N3.A3 | 0.0 | 100.00000 |
| c-Sub M ΔC1N3.A4 | | |
| c-Sub M ΔC1N3.A5 | 0.0 | 100.00000 |
| c-Sub M ΔC1N3.A6 | | |

B

INHIBITORS OF AMYLOID PRECURSOR PROTEIN PROCESSING

BACKGROUND OF THE INVENTION

1. Field of the Invention

The present invention relates to a method of using a compound as an inhibitor for cleavage of amyloid precursor protein (APP) by β-secretase or γ-secretase, wherein the compound binds to the site within β-secretase or γ-secretase recognition and/or cleavage site of APP to block the approach by β-secretase or γ-secretase, while maintaining its activities for other substrates. Further, the present invention relates to inhibitors of amyloid precursor protein processing by β-secretase or γ-secretase, comprising the compound capable of binding to the site within β-secretase or γ-secretase recognition and/or cleavage site of APP. The invention also relates to treating the symptoms of Alzheimer's disease by applying the inhibitors to the person in need thereof.

2. General Background and State of the Art

Alzheimer's disease (AD), the most common cause of dementia in elderly people, is a complex disorder of the central nervous system clinically characterized by a progressive loss of cognitive abilities. Pathological hallmarks of AD are extracellular senile plaques, intracellular neurofibrillary tangles composed of abnormal tau paired helical filaments, loss of neurons, cerebral amyloid angiopathy, and degeneration of cerebrovasculatures in certain areas of the brain (Marti et al., Proc Natl Acad Sci USA 1998; 95(26):15809-15814; Yamada M., Neuropathology 2000; 20(1): 8-22; Yankner B A, Neuron 1996; 16(5):921-932). β-amyloid (Aβ) is the major component of senile plaques and is derived from the amyloid precursor protein by proteolytic cleavage (Vassar et al., Neuron 2000; 27(3): 419-422). Although accumulating evidence suggests that Aβ is a key causative agent of AD (Calhoun et al., Nature 1998; 395(6704):755-756; Hardy et al., Science 1992; 256(5054):184-185; Hsiao et al., Science 1996; 274(5284):99-102; Lewis et al., Science 2001; 293(5534):1487-1491; Schenk et al., Nature 1999; 400(6740):173-177; Sommer B., Curr Opin Pharmacol 2002; 2(1):87-92; Thomas et al., Nature 1996; 380(6570): 168-171), the exact mechanism of neuronal degeneration in AD is not clear. However, it is likely that multiple factors are involved in the development of the disease.

Alzheimer's disease (AD) is a progressive neurodegenerative dementia afflicting 1% of the population over age 65. A significant pathological feature, however, is an overabundance of diffuse and compact senile plaques in association and limbic areas of the brain. Although these plaques contain multiple proteins, their cores are composed primarily of β-amyloid, a 40-42 amino acid proteolytic fragment derived from the amyloid precursor protein (Selkoe D J. Cellular and molecular biology of β-amyloid precursor and Alzheimer's disease. In: Prusiner S B, Rosenberg R N, Mauro S D, et al, eds. The molecular and genetic basis of neurological disease. Boston: Butterworth Heinemann Press, 1997:601-602).

APP is a single-transmembrane protein with a 590-680 amino acid long extracellular amino terminal domain and an approximately 55 amino acid cytoplasmic tail which contains intracellular trafficking signals. mRNA from the APP gene on chromosome 21 undergoes alternative splicing to yield eight possible isoforms, three of which (the 695, 751 and 770 amino acid isoforms) predominate in the brain. $APP_{695}$ is the shortest of the three isoforms and is produced mainly in neurons. Alternatively, $APP_{751}$, which contains a Kunitz-protease inhibitor (KPI) domain, and $APP_{770}$, which contains both the KPI domain and an MRC-OX2 antigen domain, are found mostly in non-neuronal glial cells. All three isoforms share the same Aβ, transmembrane and intracellular domains and are thus all potentially amyloidogenic. The normal function of APP is currently unknown, although in neurons it has been demonstrated to be localized in synapses where it may play a role in neurite extension or memory.

APP can undergo proteolytic processing via 2 pathways. Cleavage by α-secretase occurs within the Aβ domain and generates the large soluble N-terminal APPα and a non-amyloidogenic C-terminal fragment. Further proteolysis of this fragment by γ-secretase generates yet other the non-amyloidogenic peptide p3. Alternatively, cleavage of APP by β-secretase occurs at the beginning of the Aβ domain and generates a shorter soluble N-terminus, APPβ, as well as an amyloidogenic C-terminal fragment (C99). Further cleavage of this C-terminal fragment by γ-secretase generates Aβ. Cleavage by γ-secretase or multiple γ-secretases can result in C-terminal heterogeneity of Aβ to generate Aβ40 and Aβ42.

In further detail, APP is trafficked through the constitutive secretory pathway, where it undergoes post-translational processing including a variety of proteolytic cleavage events. APP can be cleaved by three enzymatic activities termed α-, β-, and γ-secretase (FIG. 1). α-secretase cleaves APP at amino acid 17 of the Aβ domain, thus releasing the large amino-terminal fragment sAPPα for secretion. Since α-secretase cleaves within the Aβ domain, this cleavage precludes Aβ formation. Rather, the intracellular carboxy-terminal domain of APP generated by α-secretase cleavage is subsequently cleaved by γ-secretase within the predicted transmembrane domain to generate a 22-24 residue (~3 kD) fragment termed p3 which is non-amyloidogenic (Sisodia et al., Science; 248:492-5 (1990)). Alternatively, APP can be cleaved by β-secretase to define the amino terminus of Aβ and to generate the soluble amino-terminal fragment APPβ. Subsequent cleavage of the intracellular carboxy-terminal domain of APP by γ-secretase yields full-length Aβ. Carboxy-terminal cleavage of Aβ by γ-secretase results in the generation of multiple peptides, the two most common being 40-amino acid Aβ (Aβ40) and 42-amino acid Aβ (Aβ42). Aβ40 comprises 90-95% of secreted Aβ and is the predominant species recovered from cerebrospinal fluid (Seubert et al., Nature; 359:325-7 (1992)). In contrast, less than 10% of secreted Aβ is Aβ42. Despite the relative paucity of Aβ42 production, Aβ42 is the predominant species found in plaques and is deposited initially (Iwatsubo et al., Neuron; 13:45-53 (1993)), perhaps due to its ability to form insoluble amyloid aggregates more rapidly than Aβ40 (Jarrett et al., Biochemistry; 32:4693-7 (1993); Jarret et al., Cell; 73:1055-89 (1993)).

Aβ has been postulated to be a causal factor in the pathogenesis of AD. The presence of Aβ-containing amyloid plaques is necessary for the neuropathological diagnosis of AD, suggesting that these entities may be involved in the etiology of the disease. Supportive evidence for the causal role of Aβ in AD can be found in patients with Down's syndrome, who often develop AD-like symptoms and pathology after age 40 (Wisniewski et al., Neuron; 35:957-61(1985)). Down's syndrome patients produce elevated APP presumably due to an additional copy of chromosome 21 and exhibit florid AD-like amyloid plaques prior to the onset of other AD symptoms, suggesting that amyloid deposition is an initial event (Giaccone et al., Neurosci Lett; 97:232-8 (1989)). Furthermore, alterations in APP processing have been linked to a subset of familial AD patients (FAD) with autosomal dominant mutations in APP (Goate et al., Nature;

349:704-6 (1991); Citron et al., Nature; 360:672-4 (1992)), presenilin 1 (PS1; 14) and presenilin 2 (PS2; 15).

Given the evidence that altered production of Aβ may be an initial event in the development of AD, much research has focused on understanding the mechanisms by which APP is processed to generate Aβ. The main cleavage pathways appear to be conserved in both neuronal and non-neuronal cells, but the predominant intracellular sites of production and the particular products formed are cell-type dependent. Non-neuronal cells preferentially process APP via α- and γ-secretase cleavage to generate APPα and the non-amyloidogenic fragment p3. Thus, non-neuronal cells are not a significant source of Aβ under normal conditions. However, although non-neuronal cells predominantly utilize α-secretase, neurons do not rely heavily on this pathway and produce very low levels of p3 (Chyung et al., J Cell Bio; 138:671-80 (1997)). Regardless of the cell type, α-secretase cleaves APP constitutively (Sisodia et al., Science; 248: 492-5 (1990)) and is thought to occur mainly at the cell surface since APPα cannot be detected intracellularly (Chyumg et al., J Cell Bio; 138:671-80 (1997); Forman et al., J Biol Chem; 272:32247-53(1997)) and cell-surface labeled APP can be recovered as APPα in the medium (Sisodia, Proc Natl Acad Sci USA; 89:6075-9 (1992)). Cleavage by β- and γ-secretases yields Aβ3 and is also a constitutive event, as Aβ can be detected in normal brains in picomolar to nanomolar concentrations (Haass et al., Nature; 359:322-5 (1992); Seubert et al., Nature; 361:260-3 (1993)).

It can be seen that one of the ways to prevent the accumulation of β-amyloid is to prevent β-secretase and/or γ-secretase from cleaving and processing APP. However, secretases are involved in the processing of many important proteins in the organism, and therefore inhibiting secretase activity may cause undesirable side effects. Thus, inactivating β-secretase and/or γ-secretase per se is not an appealing method of preventing APP processing.

Therefore, there is a need in the art to provide a method of treating or preventing Alzheimer's Disease, and in particular inhibiting β-amyloid formation and aggregation. Further, it is desirable to develop compounds that inhibit the processing of APP only without affecting other cellular machinery. Furthermore, design of APP specific inhibitors that can bind to the β-secretase and/or γ-secretase site of APP is desirable to block the approach of these secretases avoiding the processing of other important substrates of these secretases.

SUMMARY OF THE INVENTION

The invention provides solutions to the above-mentioned problems. The present relates to a method of using a compound as an inhibitor that protects APP from cleavage by β-secretase or γ-secretase, wherein the compound binds to the site within the β-secretase or γ-secretase recognition and/or cleavage sites on APP to specifically inhibit the β-secretase or γ-secretase's activity to cleave APP, thereby inhibiting the production of Aβ, while maintaining the β-secretase or γ-secretase activities to other substrates. The compound may be selected from the group consisting of polypeptides having 4-20 amino acids, peptide mimetics, and small molecules. In one embodiment, the present invention is based on the discovery of several polypeptides that bind to the β-secretase or γ-secretase cleavage sites on APP. Particularly exemplified are various decamers, although the invention is not limited to decamers. The invention is directed to any polypeptide or peptide mimetic compound that binds to the β-secretase or γ-secretase cleavage sites on APP, including polypeptides or peptide mimetics having about 4 to 20 amino acids, in particular, about 4-15 amino acids, and further in particular 4 to 11 amino acids, and still in particular, 4-7 amino acids. Further, mimetics that cross the blood-brain barrier are also contemplated. Furthermore, the compounds to be used as drug should possess high affinity and specificity for APP, be stable, small and able to be transported across the plasma membrane with adequate solubility and hydrophobicity.

In certain respects, the present invention is directed to a polypeptide or a peptide mimetic compound which binds to the β-secretase cleavage site of amyloid precursor protein. The polypeptide or the peptide mimetic compound may contain about 4 to 20 amino acids long. The polypeptide may contain about 4 to 15 amino acids or about 4 to 10 amino acids.

The β-secretase cleavage site of the amyloid precursor protein may be located within SEVKMDAEFR (SEQ ID NO:1) sequence of APP, which is the wild-type version. However, the invention contemplates and includes non-wild type β-secretase cleavage sites, such as SEVNLDAEFR (SEQ ID NO:2), which is an exemplified mutant sequence. The cleavage products of the amyloid precursor protein having the sequence of SEVKMDAEFR (SEQ ID NO:1) or SEVNLDAEFR (SEQ ID NO:2) may be SEVKM (SEQ ID NO:3) and DAEFR (SEQ ID NO:4); or SEVNL (SEQ ID NO:5) and DAEFR (SEQ ID NO:4), respectively.

In one aspect of the invention, the polypeptide which binds to the wild type β-secretase cleavage site of amyloid precursor protein may comprise various fragments of SEFCIHLHFR (SEQ ID NO: 6), or SEFCIQIHFR (SEQ ID NO: 7). However, other polypeptides and peptide mimetic compounds thereof may be synthesized against the wild-type and non-wild type β-secretase cleavage site based on known peptide complementarity and known chemical synthesis methods. Thus, in one aspect of the invention, the polypeptide may be translated from complementary nucleic acid sequence that encodes the β-secretase cleavage site. Other peptide mimetic compounds are also contemplated in the invention based on making mutations and synthesizing an array of biomimetic compounds that are intelligently based on the peptide sequence. In the preferable embodiment, the peptide mimetic may have 6-aminohexanoic acid at N or C-terminus of the polypeptide capable of binding to the β-secretase cleavage site of APP.

The invention is further directed to a method of preventing binding between APP and β-secretase, comprising providing a compound which inhibits the interaction between APP and β-secretase such as the polypeptide or peptide mimetic compound described above. However, the compound may be any class of compound so long as it is capable of inhibiting the binding between APP and β-secretase. In the method, the compound may be provided to a mammal suffering from a disease indicated by formation of amyloid plaques.

The invention may include a method of screening for a compound which inhibits APP/β-secretase binding, comprising:

(a) contacting a compound with a sample containing APP or a fragment of APP that contains β-secretase binding site, to allow the compound to bind to the APP or a fragment of APP, wherein the compound may be selected from the group consisting of synthetic peptide libraries, phage-displayed peptide libraries, library of small molecular weight chemical compounds, and the peptide sequences predicted from hydropathic complementarity (Blalock and Smith (1985) Biochemical and Biophysical Communications 121:203-207);

(b) contacting β-secretase with the APP or a fragment of APP of step (a);

(c) measuring the level of the APP or fragment having APP/β-secretase binding site cleaved by β-secretase; and (d) determining the compound as an inhibitor against APP/β-secretase binding, when the level measured in step (c) is lowered in the presence of the compound of step (a) than in the absence thereof.

The invention may also include a method of treating Alzheimer's Disease comprising administering to a person in need thereof a therapeutically effective amount of a compound which inhibits binding between APP and β-secretase.

Further, the invention may also include a peptide mimetic compound, which mimics the activity of the polypeptide which specifically binds to the β-secretase cleavage site of amyloid precursor protein and which may be effective in inhibiting binding between the APP and β-secretase.

The present invention is also directed to a polypeptide described above that binds to β-secretase cleavage site, which is covalently linked to amino acid residues that aid in transport of the polypeptide through the cell membrane such as the blood-brain barrier. In a preferred aspect, without limitation, the amino acid residues may comprise Arginine.

In another aspect of the invention, the present invention is directed to a polypeptide which binds to γ-secretase cleavage site of amyloid precursor protein. The polypeptide may be about 4 to 20 amino acids long. The polypeptide may be about 4 to 15 amino acids or about 4 to 10 amino acids long.

The γ-secretase cleavage site of the amyloid precursor protein may be within GVVIATVIVI (SEQ ID NO:8), which is the wild-type version. However, the invention contemplates and includes non-wild type γ-secretase cleavage sites.

The polypeptide which binds to the γ-secretase cleavage site of amyloid precursor protein may comprise PQQYRCHRQR (SEQ ID NO:9) or a fragment thereof. In one aspect of the invention, the polypeptide may be translated from complementary nucleic acid sequence that encodes the γ-secretase cleavage site. However, other polypeptides and peptide mimetic compounds thereof may be synthesized against the wild-type and non-wild type γ-secretase cleavage site based on known peptide complementarity and known chemical synthesis methods. Other peptide mimetic compounds are also contemplated in the invention based on making mutations and synthesizing an array of biomimetic compounds that are intelligently based on the peptide sequence.

The invention is further directed to a method of preventing binding between APP and γ-secretase, comprising providing a compound which inhibits the interaction between APP and γ-secretase, such as a polypeptide or peptide mimetic compound described above. However, the compound may be any class of compound so long as it is capable of inhibiting the binding between APP and γ-secretase. In the method, the compound may be provided to a mammal suffering from a disease indicated by formation of amyloid plaques. Further in the method, the compound may be a polypeptide.

The invention may include a method of screening for a compound which inhibits APP/γ-secretase binding, comprising:

(a) contacting a compound with a sample containing APP or a fragment of APP that contains γ-secretase binding site, to allow the compound to bind to the APP or a fragment of APP, wherein the compound can be selected from the group consisting of synthetic peptide libraries, phage-displayed peptide libraries, library of small molecular weight chemical compounds, and the peptide sequences predicted from hydropathic complementarity (Blalock and Smith (1985) Biochemical and Biophysical Communications 121:203-207);

(b) contacting γ-secretase with the APP or a fragment of APP of step (a);

(c) measuring the level of the APP or fragment having APP/γ-secretase binding site cleaved by β-secretase; and (d) determining the compound as an inhibitor against APP/γ-secretase binding, when the level measured in step (c) is lowered in the presence of the compound of step (a) than in the absence thereof.

The invention may also include a method of treating Alzheimer's Disease comprising administering to a person in need thereof a therapeutically effective amount of a compound which inhibits binding between APP and γ-secretase.

Further, the invention may also include a polypeptide or peptide mimetic compound, which mimics the activity of the polypeptide which specifically binds to γ-secretase cleavage site of amyloid precursor protein and which may be effective in inhibiting binding between the APP and γ-secretase.

The present invention is also directed to a polypeptide described above that binds to the γ-secretase cleavage site, which is covalently linked to amino acid residues that aid in transport of the polypeptide through the cell membrane such as the blood-brain barrier. In a preferred aspect, without limitation, the amino acid residues may comprise Arginine.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1 is prior art.

In FIG. 2A, mRNA sequence of the β-secretase cleavage site of APPsw is depicted as 5'-ucugaagugaaucuggaugcagaauuccga-3' (SEQ ID NO: 10), and the anti-sense mRNA sequence of the β-secretase cleavage site of APPsw is depicted as 3'-agacuucacuuagaccuacgucuuaaggcu-5' (SEQ ID NO:11). Translation of the anti-sense RNA in 5'-3' direction predicts the polypeptide SEFCIQIHFR (SEQ ID NO:7) (c-Sub M) and translation in 3'-5' direction predicts the polypeptide RLHLDLRLKA (SEQ ID NO: 12) (Sub M-c). In FIG. 2B, mRNA sequence of the β-secretase cleavage site of APP is depicted as 5'-ucugaagugaagauggaugcagaauuccga-3' (SEQ ID NO:13), and the anti-sense mRNA sequence of the β-secretase cleavage site of APP is depicted as 3'-agacuucacuucuaccuacgucuuaaggcu-5' (SEQ ID NO:43). Translation of the antisense RNA in 5'-3' direction predicts the polypeptide SEFCIHLHFR (SEQ ID NO:6) (c-Sub W) and translation in 3'-5' direction predicts the polypeptide RLHFYLRLKA (SEQ ID NO:14) (Sub W-c).

FIGS. 3A and 3B show binding of substrate M (FIG. 3A) and substrate W (FIG. 3B) to their complementary peptides. In FIG. 3A, different amounts of complementary peptides were immobilized on plastic well and biotin-labeled Substrate M was added to the well. The bound Substrate M was determined by reaction with Steptavidin-horseradish peroxidase. Control peptide refers to a decapeptide which has an unrelated sequence. In FIG. 3B, complementary peptides were immobilized on plastic well and biotin-labeled Substrate M was added to the well. The bound Substrate M was determined by reaction with Steptavidin-horseradish peroxidase.

FIG. 5 shows deletion mutants of APPsw inhibitor used in the experiment. c-SubM (SEFCIQIHFR) (SEQ ID NO:7), c-SubM ΔN1 (EFCIQIHFR) (SEQ ID NO:15), c-SubM ΔN2 (FCIQIHFR) (SEQ ID NO:16), c-SubM ΔN3 (CIQIHFR) (SEQ ID NO:17), c-SubM ΔN4 (IQIHFR) (SEQ ID NO:18), c-SubM ΔN5 (QIHFR) (SEQ ID NO:19), c-SubM ΔC1 (SEFCIQIHF) (SEQ ID NO:20), c-SubM ΔC2 (SEFCIQIH) (SEQ ID NO:21), c-SubM ΔC3 (SEFCIQI) (SEQ ID NO:22), c-SubM ΔC4 (SEFCIQ) (SEQ ID NO:23), c-SubM ΔC5 (SEFCI) (SEQ ID NO:24), c-SubM ΔC6 (SEFC) (SEQ ID NO:25), c-SubM ΔC7 (SEF).

FIG. 6 shows the effects of various deletion peptides on substrate cleavage.

FIG. 20A shows activity in HT22 (5.55 mg/ml)—immortalized mouse hippocampal neuron and PC12 (7.61 mg/ml)—rat adrenal pheochromocytoma. FIG. 20B shows activity in HN33 (5.95 mg/ml)—mouse hippocampal neuron+neuroblastoma and N2a (3.65 mg/ml)—mouse neuroblastoma.

FIGS. 23A-23B show Alanine scanning data for c-SubM ΔC1N3. FIG. 23A shows the various alanine mutants. FIG. 23B shows BACE inhibitory activity. C-SubM ΔC1N3 (CIQIHF) (SEQ ID NO:29), C-SubM ΔC1N3.A1 (AIQIHF) (SEQ ID NO:35), C-SubM ΔC1N3.A2 (CAQIHF) (SEQ ID NO:36), C-SubM ΔC1N3.A3 (CIAIHF) (SEQ ID NO:37), C-SubM ΔC1N3.A4 (CIQAHF) (SEQ ID NO:38), C-SubM ΔC1N3.A5 (CIQIAF) (SEQ ID NO:39), C-SubM ΔC1N3.A6 (CIQIHA) (SEQ ID NO:40).

Figure 1:
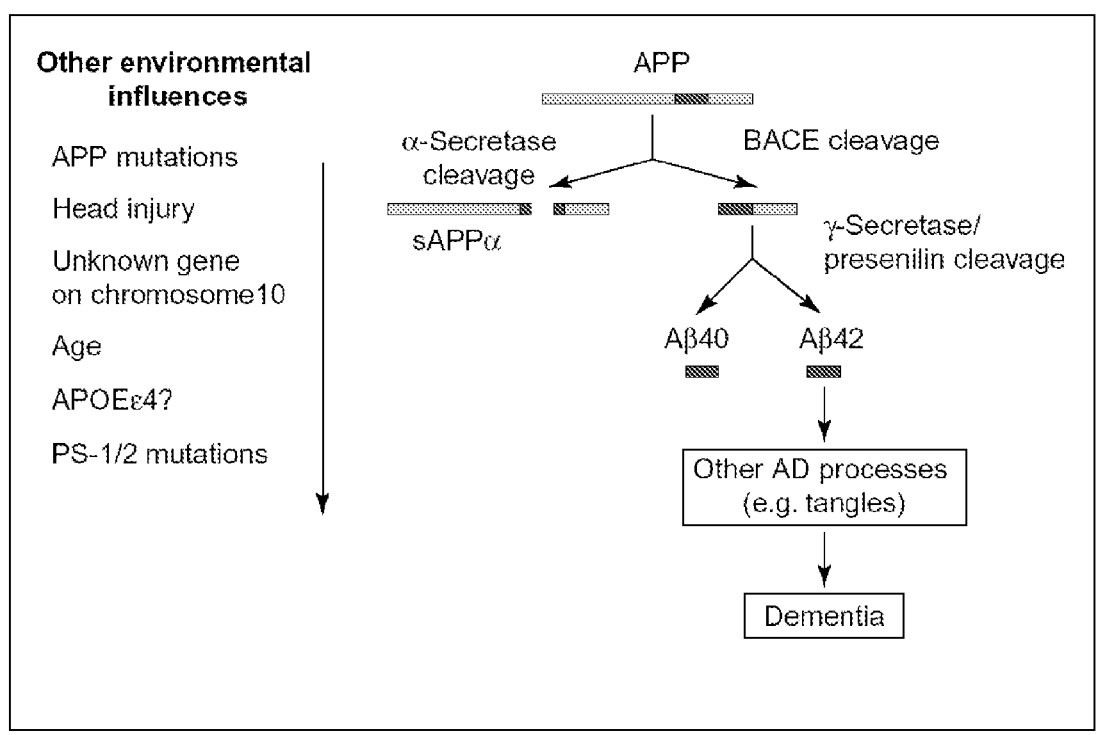
FIG. 1 shows the APP processing scheme.

As used herein, "complementary" has a meaning based upon its context of usage. For example, complementary bases or nucleotides are those characteristically forming hydrogen bonds (G-C and A-T or A-U), complementary codons nucleic acids or strands thereof are hydrogen bonded polynucleotide components of a double nucleic acid strand such of that in the classically defined double helix for example complementary amino acids usually having hydropathic complementary are those directed by members of a pair of complementary codons.

Complementary peptides or polypeptides and their related original peptide or protein are a pair of peptides directed by complementary nucleotide or amino acid sequences, and characteristically have a binding affinity between members of a pair. Polypeptides complementary to a peptide or at least a portion of a protein, for example, have a binding affinity for the peptide or protein portion. While peptide binding affinities are incompletely understood, they may, in part at least, be explained by the concept of amphiphilic secondary structure described by Kaiser et al. (Science; 223:249-255 (1984)).

The complementary polypeptide and any peptide mimetic compound thereof whose amino acid sequence is thus determined may be obtained by diverse means such as, for example, chemical synthesis, derivation from a protein or larger polypeptide containing the amino acid sequence, or, where appropriate especially for production of a naturally occurring amino acid chain, recombinant production by transforming a unicellular organism with a DNA vector to produce a transformant unicellular organism biosynthesizing the complementary polypeptide.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" is defined as an amount of compound capable of preventing binding of β- or γ-secretase to APP.

As used herein, "hydropathic complementarity", referring to the hydropathic scores (a relative measure of hydrophilicity and hydrophobicity) of amino acids is indicated in terms of low and high hydropathy corresponding to a high hydropathy. In referring to structures comprising amino acids, they are generally referred to as peptides, polypeptides or proteins, this order designating an increase in size between, for example, dipeptides, oligopeptides, and proteins containing many hundreds of amino acids.

As used herein, "inhibitor" refers to a molecule that inhibits the binding of β- or γ-secretase to APP.

As used herein, "ligand" refers to any molecule or agent, or compound that specifically binds covalently or transiently to a molecule such as a polypeptide.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "purified" or "isolated" molecule refers to biological or synthetic molecules that are removed from their natural environment and are isolated or separated and are free from other components with which they are naturally associated.

As used herein, the term "specifically binds" refers to a non-random binding reaction between two molecules, for example between a polypeptide or a peptide mimetic compound that binds to the β- or γ-secretase cleavage site on APP.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

Screening for Compounds that Bind to APP β- or γ-Secretase Cleavage Site

In one embodiment, the invention is directed to screening for a compound such as a polypeptide, a peptide mimetic, or chemical compound that inhibits binding of APP to β- or γ-secretase. It is expected that the inhibitor compound will treat persons suffering from diseases that are at least in part caused by the deposit of β-amyloid.

A fragment of APP which contains the β- or γ-secretase cleavage site may be used as a target to screen for compounds that may prevent the cleavage of this site by β- or γ-secretase. Various libraries (mixtures) may be used including synthetic peptide libraries, phage display library or chemical library to screen for compounds that bind to APP and inhibit cleavage by β- or γ-secretase, thus resulting in inhibition of production of Aβ.

Inhibitor of APP/β- or γ-Secretase Binding

In one aspect, the invention is directed to any inhibitor molecule that is capable of interacting with APP to block the binding of β- or γ-secretase to APP. In particular, the molecule should interact with the β- or γ-secretase binding domain of APP. It is understood that the inhibitor compound may impair the interaction between the APP and β- or γ-secretase by any number of biochemical or enzymatic inhibition kinetics, such as competitive, non-competitive, or uncompetitive inhibition, so long as the compound impairs the binding of APP with β- or γ-secretase and prevents cleavage at the β- or γ-secretase cleavage site. Exemplified polypeptides that bind to a 10 amino acid fragment of APP that contains the β-secretase cleavage site include without limitation, SEFCIHLHFR (SEQ ID NO:6) and SEFCIQIHFR (SEQ ID NO:7). Exemplified polypeptides that bind to a 10 amino acid fragment of APP that contains the γ-secretase cleavage site include without limitation, PQQYRCHRQR (SEQ ID NO:9).

Variant and Mutant Polypeptides

To improve or alter the characteristics of the inhibitor polypeptide, amino acid engineering may be employed. Recombinant DNA technology known to those skilled in the art can be used to create novel mutant polypeptides including single or multiple amino acid substitutions, deletions, additions, or fusion proteins. Similar mutant polypeptides can also be produced by chemical synthesis, especially for short peptides. Such modified polypeptides can show, e.g., increased/decreased activity or increased/decreased stability. In addition, they may be purified in higher yields and show better solubility than the corresponding natural polypeptide, at least under certain purification and storage conditions.

Therapeutic Composition

In one embodiment, the present invention relates to treatment for various diseases that are characterized by the formation of β-amyloid aggregates or amyloid plaque. In this way, the inventive therapeutic compound may be administered to human patients who are either suffering from, or prone to suffer from the disease by providing compounds that inhibit the cleavage of APP to β-amyloid by binding to the β- or γ-secretase cleavage site. In particular, the disease is associated with dementia, chronic neurodegenerative disorder of the brain, loss of nerve cell, particularly in the hippocampus and cerebral cortex, reduced neurotransmitters, cerebrovascular degeneration, and/or loss of cognitive ability. Further in particular, the present invention is directed to a treatment for Alzheimer's disease. Preferably, the compound crosses the blood-brain barrier.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (e.g. using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate the ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 g and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the ingredients.

Delivery Systems

Various delivery systems are known and can be used to administer a compound of the invention, e.g., encapsulation in liposomes, microparticles, microcapsules, receptor-mediated endocytosis. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. Preferably, when administering a protein, including a peptide or peptide mimetic compound of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

Mimetics

The use of peptides as drugs has some very attractive advantages. They can be made to be highly specific; their potency can usually be increased by simple amino acid substitution; and many exhibit very low toxicity. However, the present invention is also directed to peptide mimetics. In particular, the mimetic is directed to peptide mimetics that cross the blood-brain barrier. APP is cleaved by secretases inside the cells, most likely in trans-Golgi network and endosomal system (Huse et al., J. Biol. Chem. 275:33729-37 (2000); Walter et al., J. Biol. Chem. 276:14634-41 (2001)). Therefore, an inhibitor compound that is modified so that the compound is able to cross the cell membrane barrier, as well as the blood-brain barrier is encompassed by the present invention.

A peptide mimetic is defined as a non-peptide ligand that is recognized by a peptide recognition site. Such mimetics may be structurally different from the peptides. A well-known example of a peptide mimetic is morphine. This natural opioid alkaloid is a mimetic of β-endorphin, a peptide present in the human body. While this definition of a peptide mimetic characterizes a mimetic as a non-peptide ligand, many structures exist that are somewhere in between a true peptide, which is composed of natural amino acids, and a peptide mimetic. Most compounds within the spectrum of the definition are considered peptide mimetics as well. For example, a tripeptide composed exclusively of non-natural elements can be considered a peptide mimetic. Several HIV protease inhibitors are considered peptide mimetics, although they possess amide bonds and amino acids. The debate on what constitutes a peptide mimetic is still on-going, however a person of skill in the art is able to distinguish between a mimetic and a peptide. Peptide mimetics can generally be considered as improved versions of peptides. Chemical modifications on a peptide, such as the reduction of a peptide bond, can increase its enzymatic stability. Incorporating unnatural amino acids can also enhance both activity and selectivity of the peptide. The more a peptide is altered structurally and/or chemically, the more it becomes a true peptide mimetic.

Peptide mimetics including peptides, proteins, and derivatives thereof, such as peptides containing non-peptide organic moieties, synthetic peptides which may or may not contain amino acids and/or peptide bonds, but retain the structural and functional features of a peptide ligand, and peptoids and oligopeptides which are molecules comprising N-substituted glycine, such as those described by Simon et al., Proc. Natl. Acad. Sci. USA 89:9367 (1992); and antibodies, including anti-idiotype antibodies.

In another aspect of the invention, the inventive compound of the invention may be made by synthetically introducing a variety of optional compounds, such as scaffolds, turn mimetics, and peptide-bound replacements. Syntheses of amino acids to the use of a variety of linear and heterocyclic scaffolds in place of the peptide backbone may be used. Chemical procedures and methods include the transient protection of charged peptides as neutral prodrugs for improved blood-brain penetration and the replacement of peptide bonds with groups such as heterocyclic rings, olefins and fluoroolefins, and ketomethylenes.

Hydropathic Complementarity of Amino Acid Sequence

According to the principle hydropathic complementarity of amino acids, the amino acid deduced by an antisense code (either 5'→3' or 3'→5' direction) is generally antipathic, that is, a hydrophobic amino acid sequence can be deduced from a code for a hydrophilic amino acid sequence, vice versa (Blalock and Smith, Biochem. Biophys. Res. Commun. 121:203-207 (1984); U.S. Pat. No. 4,863,857 (1989); U.S. Pat. No. 5,077,195 (1991), the contents of which are incorporated by reference herein in their entirety in particular with regard to explaining and providing evidence for hydropathic complementarity.). The peptides, which are designed by the hydropathic complementary approach, show inverse hydropathic relationship to the peptides encoded by sense mRNA, and the designed peptide binds target protein with specificity and high affinity (Bost et al., Proc. Natl. Acad. Sci. USA 82:1372-1375 (1985)). There are several examples that demonstrate successful application of this approach. Antagonists of various proteins such as ACTH, ribonuclease S peptide, c-Raf protein, fibronectin, insulin, and 1-chain of fibrinogen were developed based on this approach (Bost et al. Proc. Natl. Acad. Sci. USA 82:1372-1375 (1985); Shai et al. Biochemistry 26:669-675 (1987); Fassina et al. J. Biol. Chem. 264: 11252-11257 (1989): Brentani et al. Proc. Natl. Acad. Sci. USA 85:364-367 (1988); Knutson J. Biol. Chem. 263:14146-14151 (1988): Pasqualini et al. J. Biol. Chem. 264:14566-14570 (1989), incorporated by reference herein in their entirety.).

In one embodiment of the present invention, four HC decapeptides targeted to either wild type APP or APPsw may be designed. Interestingly, only the HC peptide c-Sub M (SEFCIQIHFR), derived from the non-coding strand of mutant substrate (Sub M) DNA, binds to Sub M appreciably but not the other HC peptides. c-Sub M may also have high binding activity for the wild type substrate (Sub W) as well. Therefore, there is possibility that c-Sub M or any compounds derived from c-Sub M may inhibit production of Aβ from wild type APP in cells. This may be an important consideration since AD patients having Swedish mutations in APP are rare, less than 1% of total AD patients. c-Sub M may also inhibit cleavage of Sub M as well as Sub W (wild type substrate) by rhBACE1 in vitro. c-Sub M apparently does not bind to rhBACE1. In an ELISA assay, it may be observed that rhBACE1 does not bind to the immobilized c-Sub M.

As mentioned above, one of the major benefits of developing APP targeted inhibitor is minimizing side effect. Such inhibitor should have preference for APP over other BACE1 substrates. However, on the contrary to the expectation, an HC peptide for APP also binds to Sub-ST6Gal1, a substrate of BACE1, and inhibits cleavage of both of Sub M and Sub-ST6Gal1 by BACE1 in vitro. Nevertheless, the HC peptide appears to have preference for inhibition of the cleavage of APP than ST6Gal1. There appears to be no apparent consensus sequences for the β-cleavage sites of different BACE1 substrates: APP (SEVKM/DAEFR), APPsw (SEVNL/DAEFR), ST6Gal1 (EALTL/QAKEF) (13), and PSGL-1 (MAASNL/SVNYPV) (14). However, it is possible that the different sequences at the β-cleavages sites provide similar chemical and structural environment to be recognized by BACE1 and by the same HC peptide.

It is found that c-Sub M does not enter the cells and hence does not inhibit the processing of APP in cells. Therefore, series of deletions may be made from either side of c-Sub M in order to identify the core sequence and also in hope that a shorter peptide sequence may be active in the cells. It is also found that the hexapeptide, CIQIHF (c-Sub M ΔN3C1), maintains much of the original activity of c-Sub M. CIQIHF may also not show inhibitory activity in the cells. 6-Aminohexanoic acid was added at N-terminus of the peptide to increase the lipophilicity. Even though the addition of 6 carbon chains decreased inhibitory activity of CIQIHF in vitro, the modified peptide inhibited production of Aβ as well as the accumulation of APP cleavage product, CTFβ, in the treated cells at μM concentrations. The results clearly demonstrate that cell-permeable peptidomimetics of HC peptides can be potential inhibitors of APP processing.

The approach described in this invention report for development of APP-specific inhibitors will provide new opportunity for development of the drugs that can be used for prevention and treatment of AD with minimal side effects.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Peptides that Bind to the β-Secretase Cleavage Site of APP

Figure 2A:
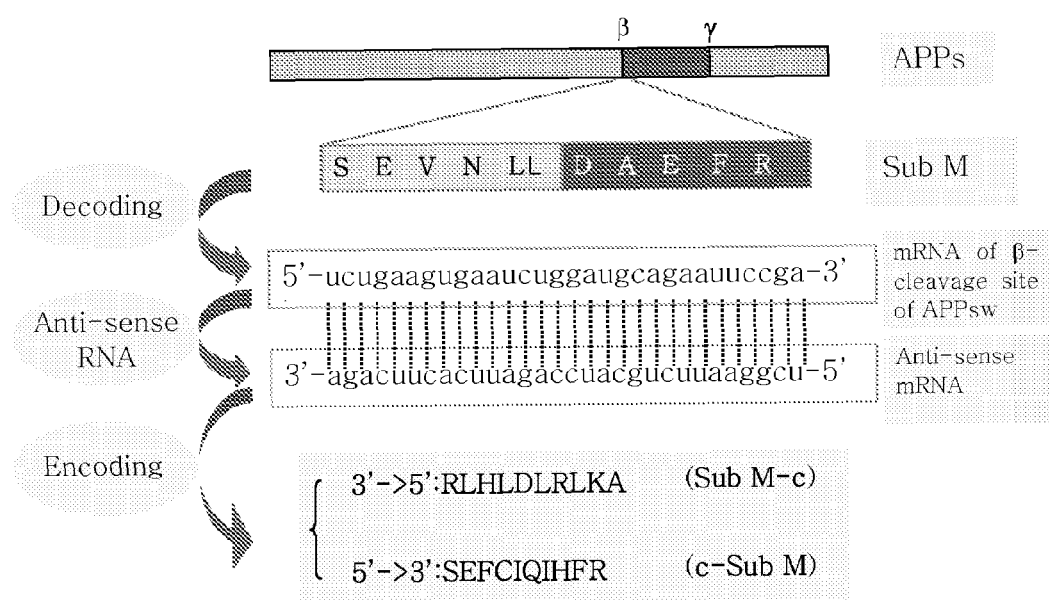
FIGS. 2A and 2B show processes of obtaining complementary peptides for Swedish mutant type APP (FIG. 2A) and wild-type APP (FIG. 2B).
Figure 2B:
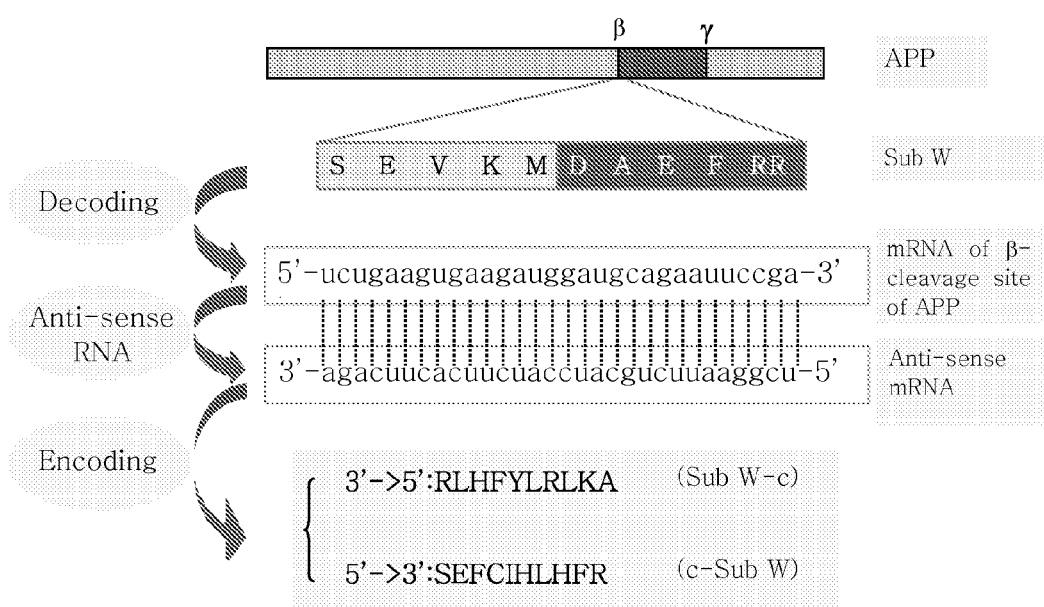

Decamer peptide sequences that contain the cleavage site of APP by β-secretase were used. The sequence is as follow: SEVKMDAEFR (SEQ ID NO: 1). This wild type peptide sequence is called Substrate W. β-secretase cleaves the peptide bond between M and D and releases the following cleavage products: SEVKM (SEQ ID NO: 3) and DAEFR (SEQ ID NO: 4). The Swedish mutant of APP (APPsw) is cleaved by β-secretase at much higher rate than normal APP. The decamer sequence containing the cleavage site of APPsw by β-secretase is as follows: SEVNLDAEFR (SEQ ID NO: 2) (FIG. 2). This mutant peptide is labeled Substrate M.

It was previously reported that in some cases, the peptides (complementary peptide) derived from anti-sense mRNA of a target peptide can bind to the target peptide (Blalock, J. E. and Smith, E. M. Biochem. Biophys. Res. Commun. 121, 203-207 (1984); Gho, Y. S. and Chae, C.-B. J. Biol. Chem. 272, 24294-24299 (1997), which are incorporated by reference in their entirety). Based on this report, we designed four peptides. The anti-sense sequences were deduced from the mRNA sequences corresponding to the two decamer substrate peptides. Genetic codes were derived from the anti-sense RNA by reading the sequences either in 5'→3' or 3'→5' directions. The following decamer peptide sequences were obtained: SEFCIHLHFR (c-Sub W, SEQ ID NO:6) and RLHFYLRLKA (Sub W-c, SEQ ID NO:14) from substrate W. From Substrate M, the following two peptides were derived: SEFCIQIHFR (c-Sub M, SEQ ID NO:7) and RLHLDLRLKA (Sub M-c, SEQ ID NO:12) (FIG. 2). These peptides are collectively called complementary peptides.

Figure 3A:
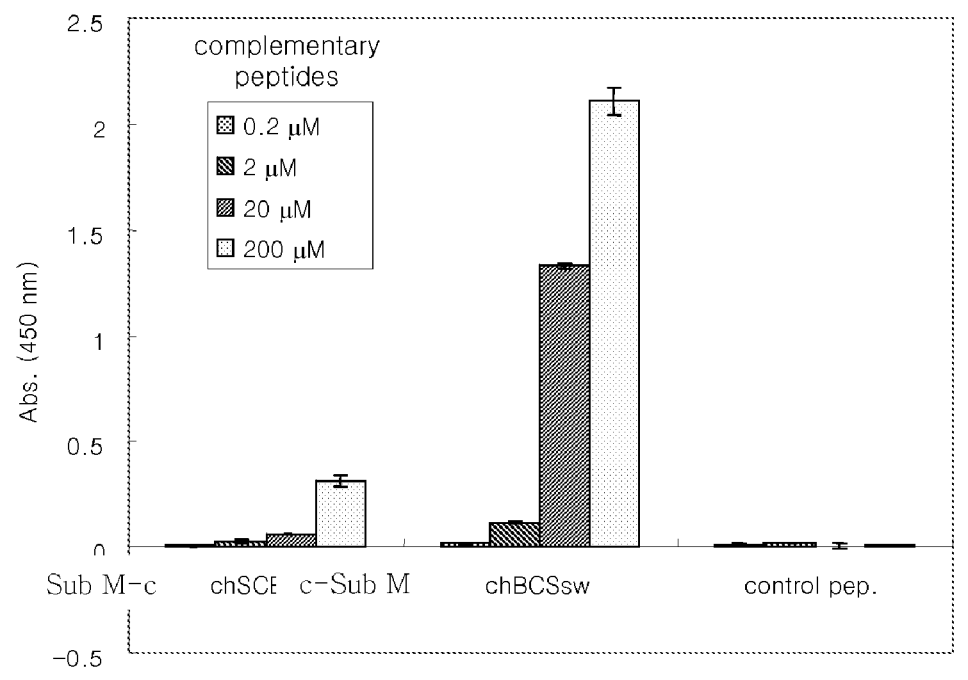
Figure 3B:
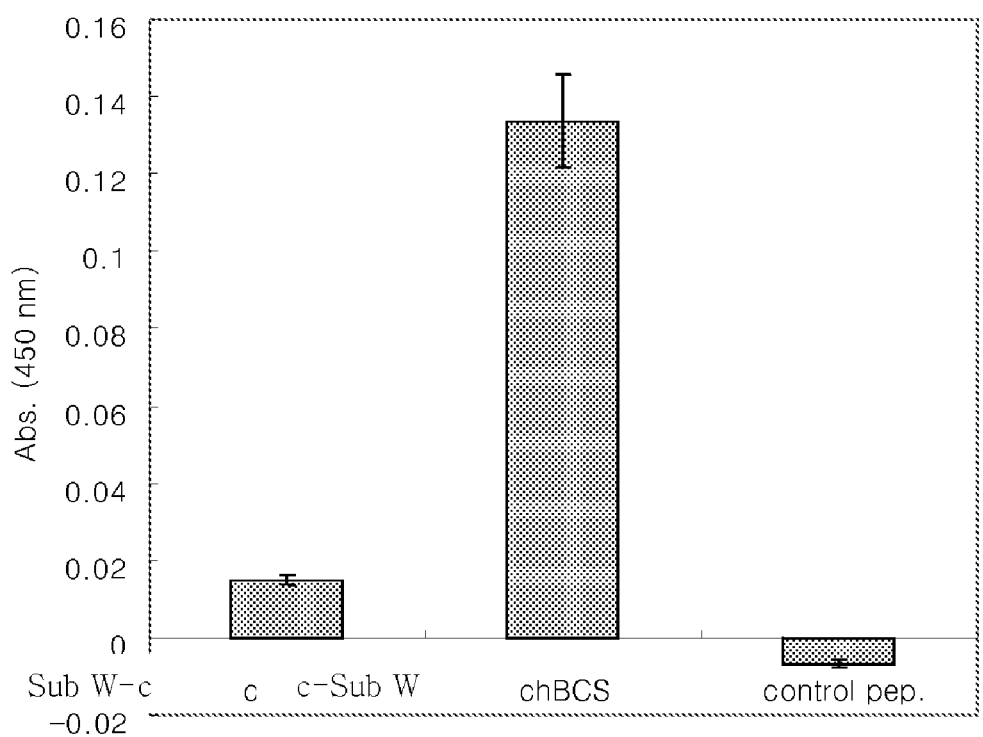
Figure 4:
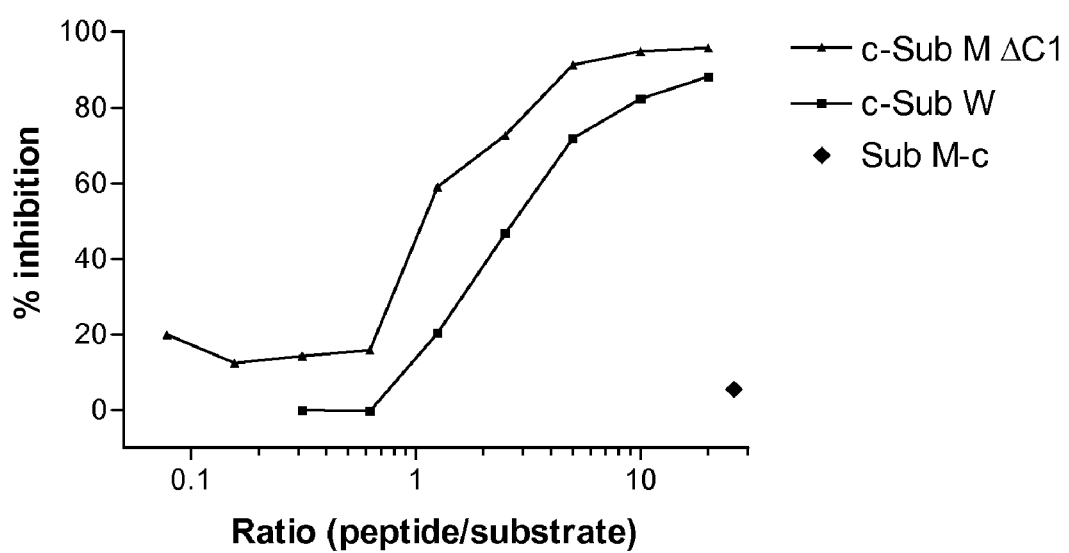
FIG. 4 shows inhibition of cleavage of Substrate M by β-secretase by complementary peptides. c-SubM CΔ1 refers to deletion of one amino acid from the C-terminus of c-SubM.

The two complementary peptides, c-Sub W and c-Sub M bind to Substrate W and M, respectively (FIG. 3) and both inhibit cleavage of the Substrate M by β-secretase (FIG. 4). Sub W-c and Sub M-c do not bind to the substrate (FIG. 3) and do not inhibit cleavage of Substrate M (FIG. 4). In our experiment, we used Substrate M mostly due to its easy cleavage by β-secretase.

Example 2

Binding of Substrates to the Complementary Peptides

Complementary peptides (0.2, 2, 20, and 200 μM) were dissolved in phosphate buffered saline (PBS) (pH 7.4) and fixed to microtiter wells for 5 hr at 37° C. The wells were blocked with blocking buffer (3% BSA/PBS) for 1 hr at 37° C. Either N-terminally biotinylated Substrate W or M (20 μM) in blocking buffer was added and incubated for overnight at 4° C. Streptavidin-horseradish peroxidase in blocking buffer was added to detect resulting bound substrates. The plate was incubated for 2 hr at room temperature (RT), followed by addition of 3, 3', 5,5'-tetramethyl-benzidine (TMB) as substrate for horseradish peroxidase for color reaction.

In particular, for Substrate W, complementary peptides (200 μM) dissolved in phosphate buffered saline (PBS) (pH 7.4) were chemically coupled to Reacti-Bind Maleic Anhydride Activated Polystyrene wells (Pierce Biotechnology, Inc.) for overnight at room temperature (RT). Remaining active sites of the plate were inactivated by adding ethanolamine (1 M) for 1 hr at RT. The wells were blocked with blocking buffer (3% BSA/PBS) for 1 hr at RT. N-terminally biotinylated Substrate W (20 μM) in blocking buffer was added and incubated for 3 hr at RT. Streptavidin-horseradish peroxidase in blocking buffer was added to detect resulting bound substrates. The plate was incubated for 2 hr at room temperature (RT), followed by addition of 3,3',5,5'-tetramethyl-benzidine (TMB) as substrate for horseradish peroxidase for color reaction.

Example 3

Fluorometric Assay for the Cleavage of Substrates by β-Secretase

This assay system utilizes fluorescence resonance energy transfer (FRET) technology. Substrate M was synthesized with two fluorophores, a fluorescent donor and a proprietary quenching acceptor (purchased from a commercial source, R&D Systems). The donor fluorescence energy is significantly quenched by the acceptor. Upon cleavage of substrate by β-secretase, the fluorophore is separated from the quenching group, restoring the full fluorescence yield of donor.

Substrate labeled with fluorophores will be called F-Substrate M (R&D Systems). Recombinant human β-secretase will be called rhBACE (recombinant human β-site APP cleavage enzyme) (purchased from R&D systems).

F-Substrate M (20 μM) was preincubated with varying concentrations of complementary peptides in assay buffer (0.1 M NaOAc, pH 4.0) for 1 hr at RT. rhBACE (70 nM) in assay buffer was added. Cleavage by rhBACE was detected by reading emitted fluorescence level.

Example 4

HPLC Analysis of the Cleavage of Substrates by β-Secretase

Substrate M (100 μM) was preincubated with complementary peptides (2.6 mM) in assay buffer (100 μl) overnight at RT. rhBACE (140 nM) in assay buffer was added and incubated for 11 hr at RT. Cleavage products of Substrate M by rhBACE were quantitated after separation by C-18 reversed-phase column chromatography (GRACE VyDAC).

Example 5

Effect of Deletions on Inhibitory Activity of the Complementary Peptides

Figure 6:
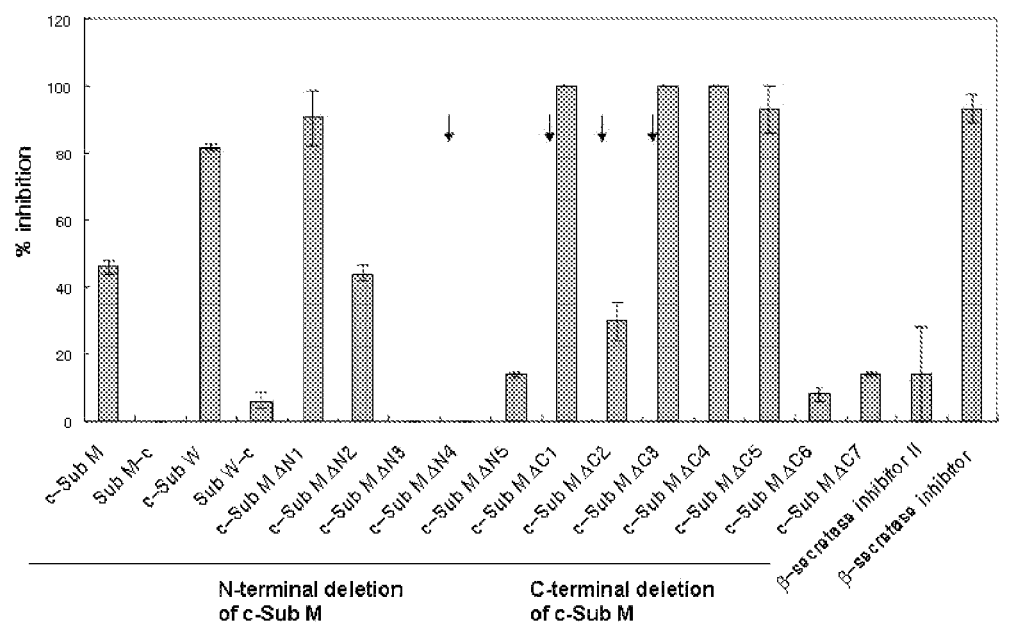
Figure 7:
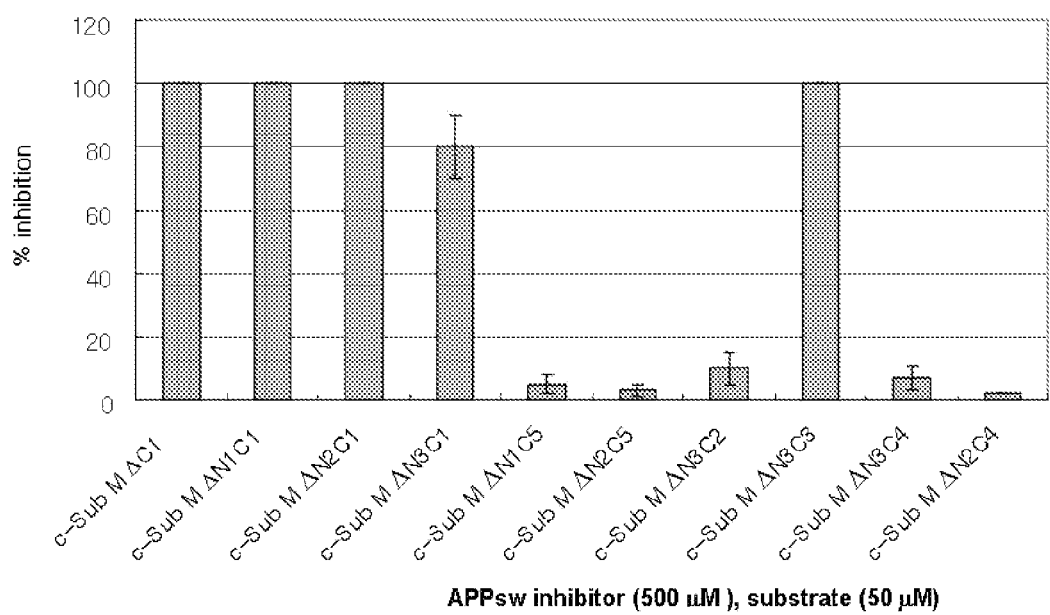
FIG. 7 shows the inhibitory activities of the additional peptides with terminal deletions on β-secretase cleavage.

So far we have focused on c-Sub M peptide. Serial deletions were made from N-terminus or C-terminus of c-Sub M (FIG. 5), and we investigated effect of the deletions on the cleavage of Substrate M. The optimum peptide/substrate ratio for inhibition on the cleavage of substrate was determined by observing the inhibition percentage at various peptide/substrate ratios (FIG. 4). Subsequently, the inhibitory activity of the deletion peptides were tested at 10 inhibitor/substrate ratio and the concentration of the Substrate M was 50 μM. Deletion of the first two amino acids from the N-terminus had little effect on the activity and deletion of five amino acids from the C-terminus of c-Sub M had little effect on the inhibitory activity (FIG. 6). Further deleted peptides were tested for inhibitory activity on the cleavage of Substrate M (FIG. 7). Five of ten tested peptides showed considerable inhibitory activity. C-Sub MΔN3C1 (hexa peptide) and C-Sub MΔN3C3 (tetra peptide) had considerable inhibitory activity.

Example 6

Concentration Dependent Inhibitory Activity of the Complementary Peptides

Figure 8:
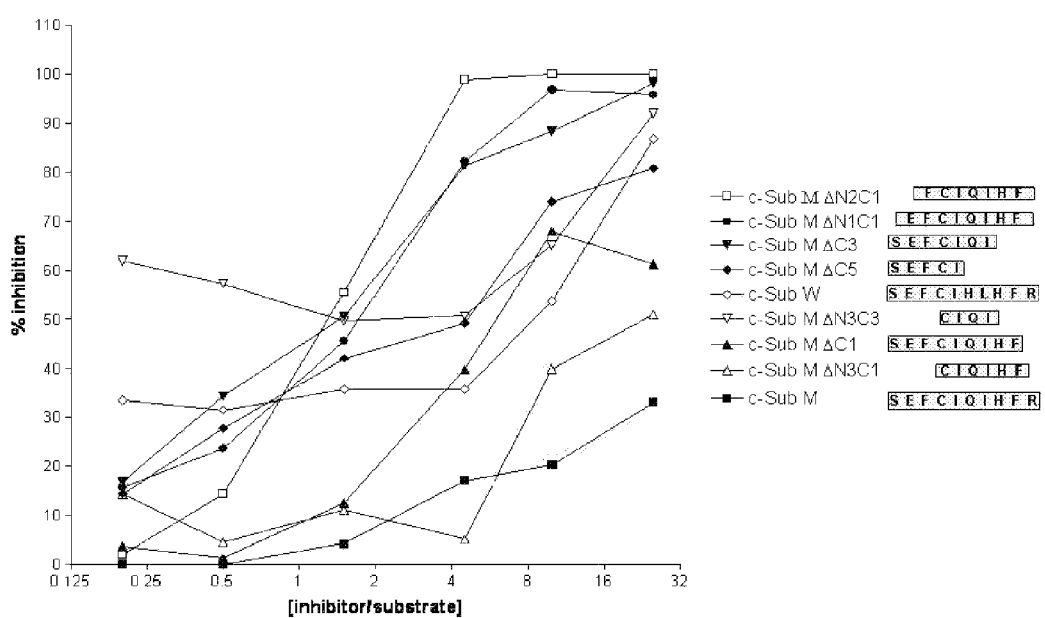
FIG. 8 shows concentration dependent inhibitory activities of various peptides tested. c-SubM ΔN2C1 (FCIQIHF) (SEQ ID NO:26), c-SubM ΔN1C1 (EFCIQIHF) (SEQ ID NO:27), c-SubM ΔC3 (SEFCIQI) (SEQ ID NO:22), c-SubM ΔC5 (SEFCI) (SEQ ID NO:24), c-SubW (SEFCIHLHFR) (SEQ ID NO:6), c-SubM ΔN3C3 (CIQI) (SEQ ID NO:28), c-SubM ΔC1 (SEFCIQIHF) (SEQ ID NO:20), c-SubM ΔN3C1 (CIQIHF) (SEQ ID NO:29), c-SubM (SEFCIQIHFR) (SEQ ID NO:7).

The above-mentioned peptides that have inhibitory activity were tested at various concentrations for their inhibitory activities on their mutant substrate Substrate M (FIG. 8). In general, based on the inhibitory activity, the peptides may be divided into three major groups: (1) the most active group including FCIQIHF (SEQ ID NO:26), EFCIQIHF (SEQ ID NO:27) and SEFCIQI (SEQ ID NO:22); (2) the group with medium activity including SEFCI (SEQ ID NO:24), SEFCIHLHFR (SEQ ID NO:6), which shows anomalous curve possibly due to aggregation and which is a complementary peptide for the wild type substrate, and CIQI (SEQ ID NO:28), which shows anomalous curve possibly due to aggregation; and (3) the group with less activity including CIQIHF (SEQ ID NO:29) and SEFCIQIHFR (SEQ ID NO:7). The results indicate that the inhibitory activities of the peptides correlate with their concentrations showing increased inhibitory activities as the concentrations of the peptides increase.

Example 7

Binding of Complementary Peptides to Both Wild Type (Sub W) and Mutant Type Substrates (Sub M)

Figure 9A:
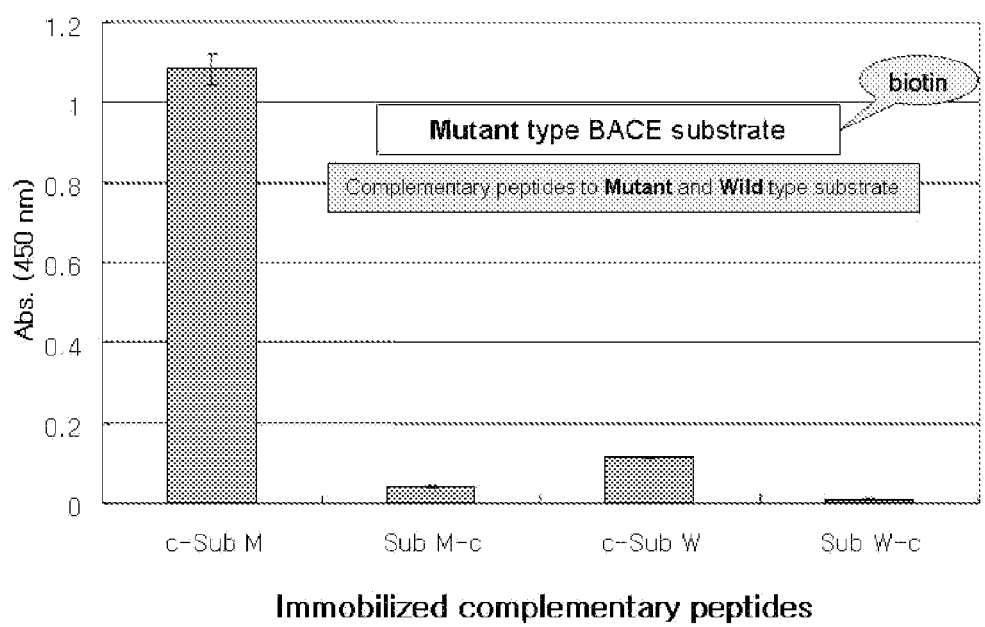
FIGS. 9A and 9B show binding between the complementary peptides and SubM and binding between the complementary peptides and SubW, respectively.
Figure 9B:
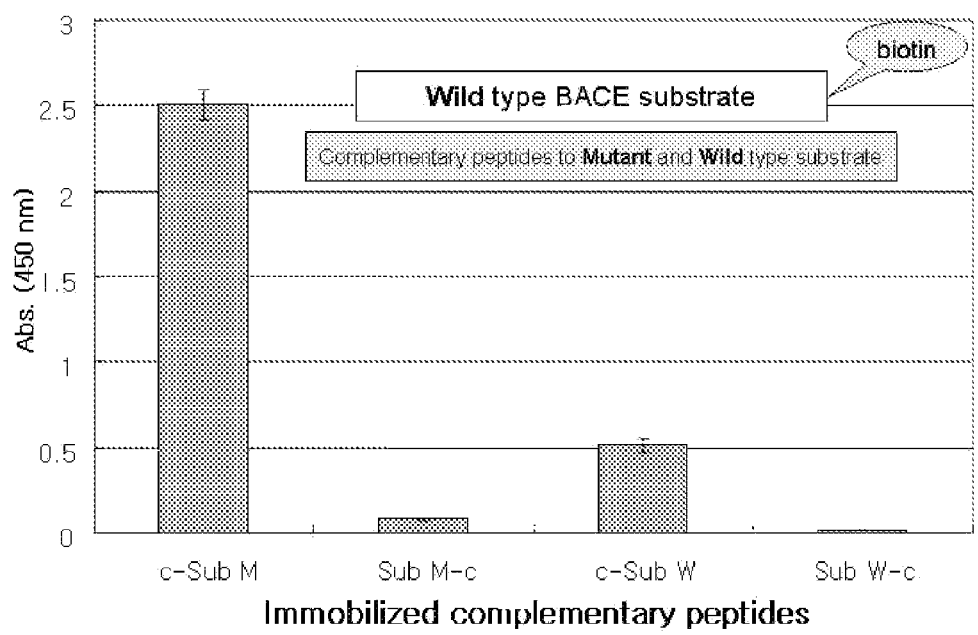

To test their binding capability, the complementary peptides were immobilized on a plate and biotin labeled substrate was applied and then after washing, the presence and amount of the bound substrate was determined. FIG. 9A shows that the complementary peptide c-Sub M binds its substrate Sub M. FIG. 9B shows that the complementary peptide c-Sub M also binds the wild type substrate Sub W efficiently. Therefore, the complementary peptide for mutant substrate binds to both the wild type and the mutant substrates.

Example 8

Cell Based Assay System

Figure 10:
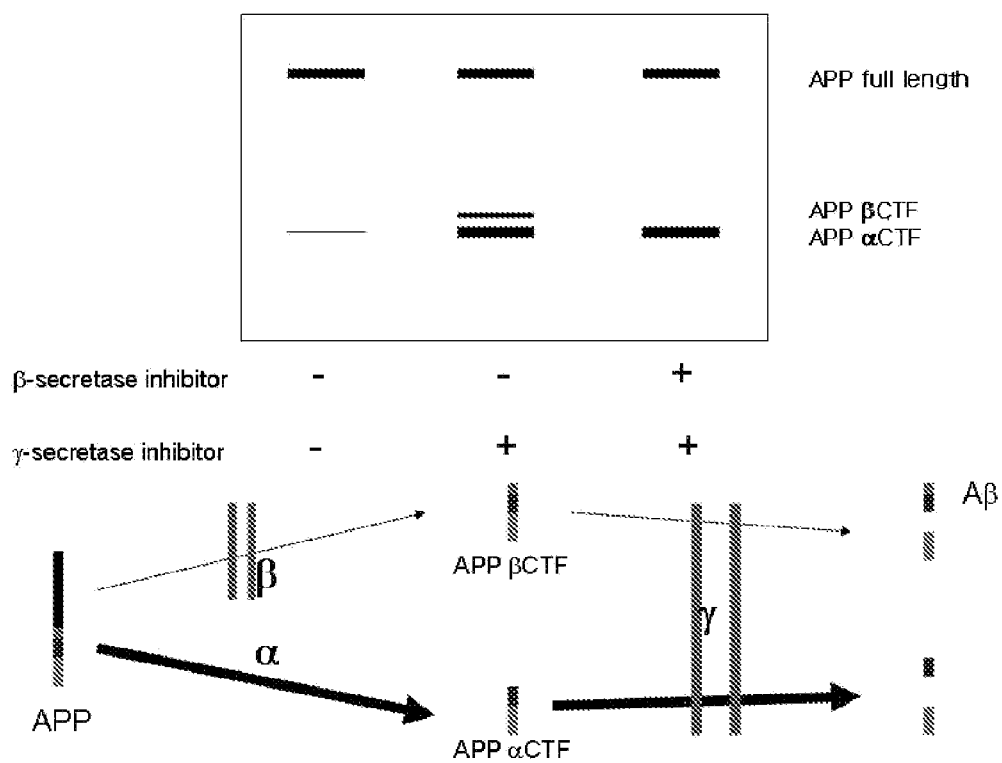
FIG. 10 describes cell based assay system to be used for determination of inhibitory activities of the complementary peptides.

In the neuronal cells of the brain, APP is processed by α-secretase or β-secretase. To investigate the effects of the inhibitors on the cell, a cell based assay system was developed as described in FIG. 10. C-terminal fragment of APP remaining on the cell membrane was detected by Western blot. The resulting C-terminal fragments, αCTF or βCTF are further processed by γ-secretase. However, if the cells are treated with the γ-secretase inhibitor, this processing is blocked. As a result, αCTF or βCTF accumulate in the cell. If β-secretase inhibitor or APP inhibitor is added, this processing is blocked and βCTF disappears.

Example 9

APP Inhibitor Activity on HEK293-APP Cells

Figure 11:
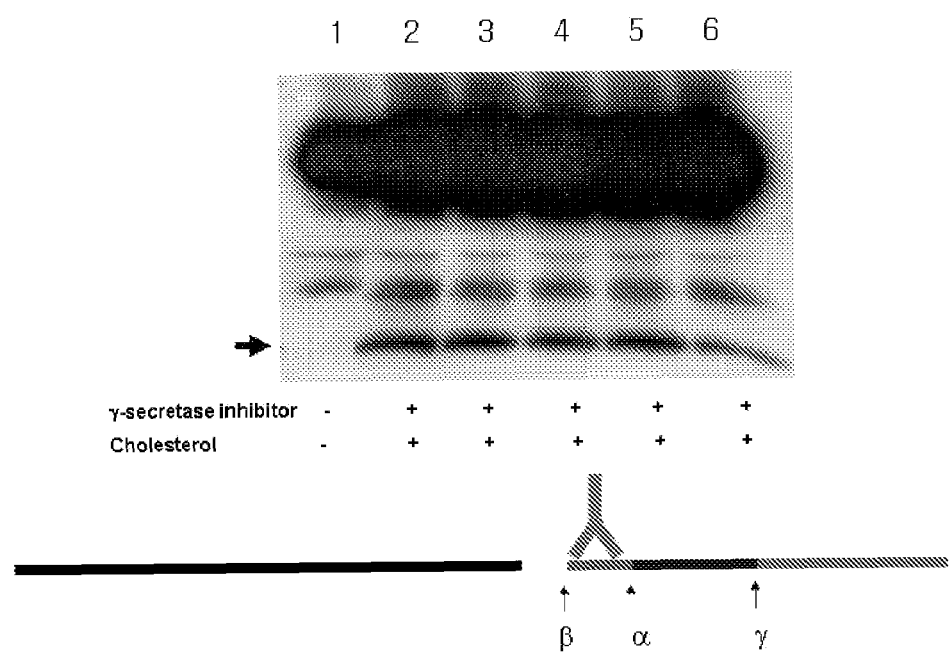
FIG. 11 shows the effects of the APP inhibitor peptides on HEK293-APP cells. Whole cell extracts were loaded. 16E10 antibody detects N-terminal of Aβ. Lanes 1.Control cells; 2.c-Sub M; 3.c-Sub M ΔC6; 4.c-Sub M ΔN1C1; 5.Control cells; 6.β-secretase inhibitor (commercial, peptide based).

To test APP inhibitor activities in cells, three complementary peptides, c-Sub M, c-Sub MΔC6, and c-Sub MΔN1C1, which show high absorbance in binding test, were added to whole cell extracts of HEK293-APP cells (Lanes 2, 3, and 4 in FIG. 11). In addition, γ-secretase inhibitor and cholesterol were added to the cells to increase βCTF level. Commercially available peptide-based β-secretase inhibitor was included as control (Lane 6, FIG. 11). To detect the N-terminal fragment of β-amyloid which is a product of APP processing, 6E10 antibody was employed. As shown in FIG. 11, none of the inhibitors tested showed inhibitory activity on APP processing including the commercially available peptide-based β-secretase inhibitor. Recently, it has been reported that the commercially available peptide-based inhibitor had to be linked to an oligoarginine transporter peptide to have inhibitory activity against cells. Therefore, mimetic approach is adopted to produce cell permeable analogs. (Chang et al. J. Neurochemistry 2004; 89:1409-1416).

Example 10

APP Inhibitor Activity on HEK293-APPsw Cells

Figure 12:
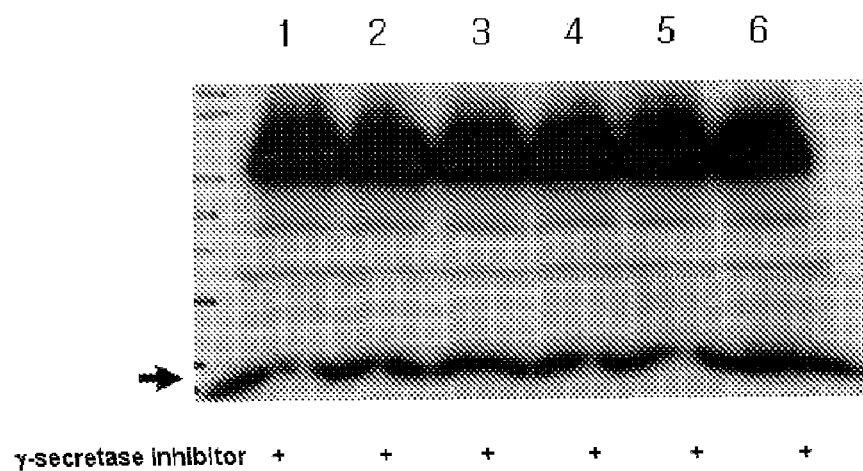
FIG. 12 shows the effects of the APP inhibitor peptides on HEK293-APPsw cells. Whole cell extracts were loaded. 16E10 antibody detects N-terminal of Aβ. Lanes 1.Blank; 2.c-Sub M ΔC1; 3.c-Sub M ΔC5; 4.c-Sub M ΔN2C1; 5.c-Sub M ΔN3C3; 6. β-secretase inhibitor.

Similarly to the results shown in Example 9, the peptide inhibitors tested on HEK293-APPsw cells showed no inhibitory activity on APP processing as the levels of βCTF detected by 6E10 antibody stayed the same in the presence of the peptide inhibitors (FIG. 12). These results shown in FIGS. 11-12 suggest that these APP inhibitors have no activity on cells because they cannot pass through the cell membrane.

Example 11

APP Inhibitor-$R_9$ Activity on rhBACE1 and Fluo-Sub M System

To overcome the problem of APP inhibitor's inability to penetrate across the cell membrane, APP inhibitors were coupled with oligo-arginine ($R_9$ means 9 Arginines), which is known to be a transporter peptide. These coupled peptides were labeled with FITC (Fluorescein isothiocyanate) using a linker AHX (aminohexanoic acid) to investigate whether the inhibitors pass through the cell membrane. FITC-AHX-c-Sub M-$R_9$ and FITC-AHX-c-Sub MΔN1C1-$R_9$ were made.

Figure 13:
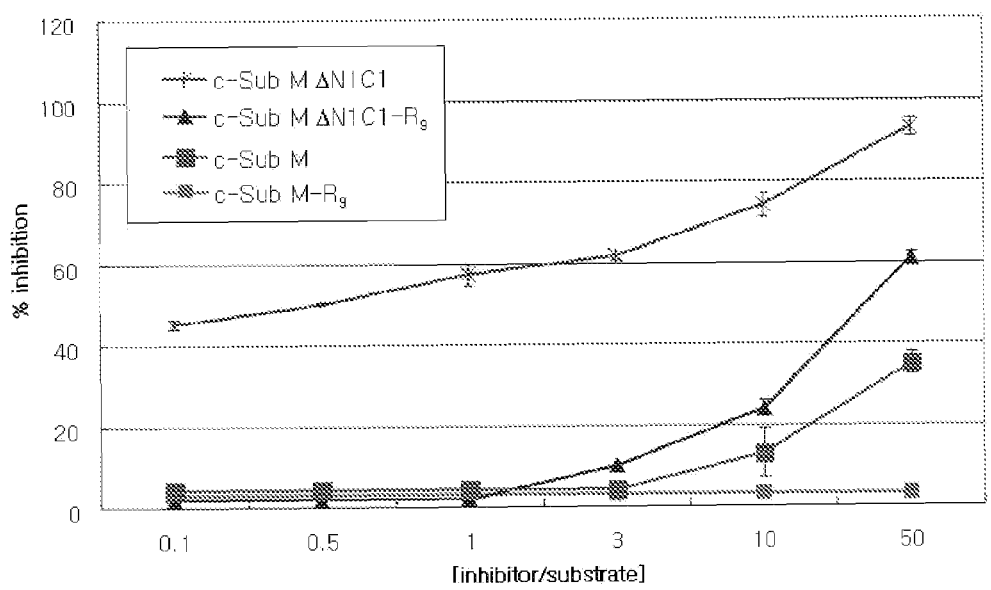
FIG. 13 shows the activities of APP inhibitor-$R_9$ on rhBACE1 and fluo-Sub M system.

To test the inhibitory activities of these oligoarginine-coupled APP inhibitors, FRET (fluorescence resonance energy transfer) enzyme assay system was used. As shown in FIG. 13, c-Sub MΔN1C1-$R_9$ showed less inhibitory activity compared to its counterpart inhibitor c-Sub MΔN1C1 lacking $R_9$. C-Sub M-$R_9$, especially showed no inhibitory activity. These results indicate that coupling of oligoarginine to APP inhibitors significantly decreases inhibitory activity.

Example 12

Figure 14:
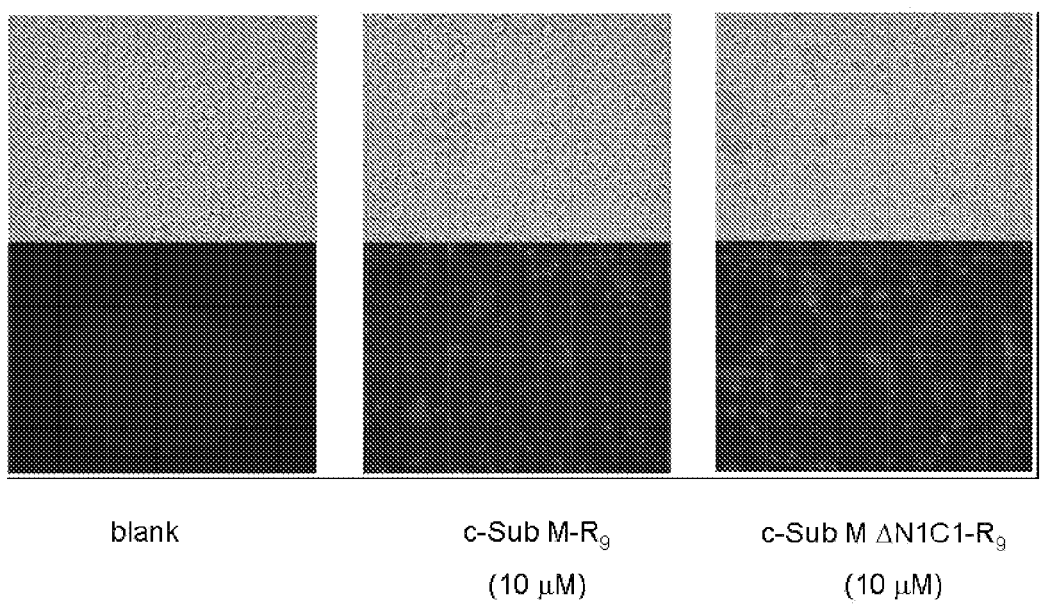
FIG. 14 shows the result of APP inhibitor-$R_9$ transport assay indicating the transportation of the oligoarginine-coupled APP inhibitors into the cells.

APP Inhibitor-$R_9$ Transport Assay and APP Inhibitor-$R_9$ Activity on 293-APP Cells Oligo-arginine coupled APP inhibitors that were labeled with FITC were added to HEK293-APP cells to see whether the peptides pass through the cell membrane. As shown in FIG. 14, the oligoarginine-coupled APP inhibitors were transported into the cells.

Figure 15:
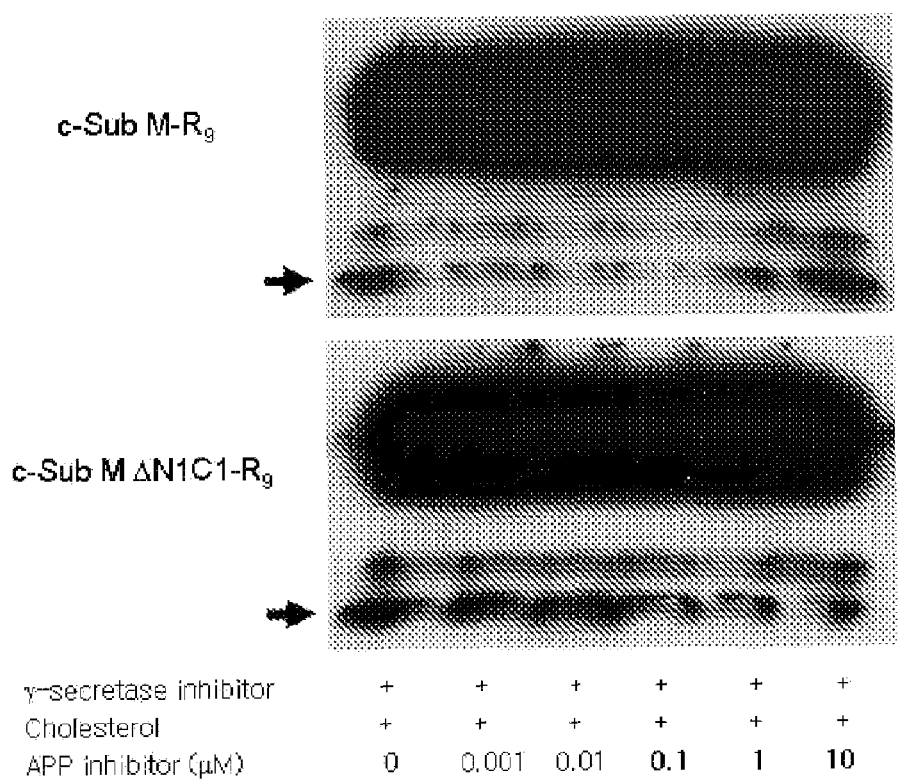
FIG. 15 shows the activities of APP inhibitor-$R_9$ on 293-APP cells.

After confirming the ability of the oligo-arginine coupled APP inhibitors to enter the cells, the inhibitors were applied to HEK293-APP cells overexpressing APP to test their inhibitory activities on APP processing. FIG. 15 shows that c-Sub M-$R_9$ has some inhibitory activity at low concentration, but no inhibitory activity was observed at 10 μM (upper panel). c-Sub MΔN1C1-$R_9$ showed inhibitory activity in a concentration dependent manner. This inhibitor started to show significant inhibitory activity beginning from 0.1 μM (lower panel). These results indicate that oligo-arginine coupled complementary peptides may be used as APP-specific inhibitors in the APP cells.

Example 13

Specificity of Complementary Peptides APP Inhibitor

Figure 16:
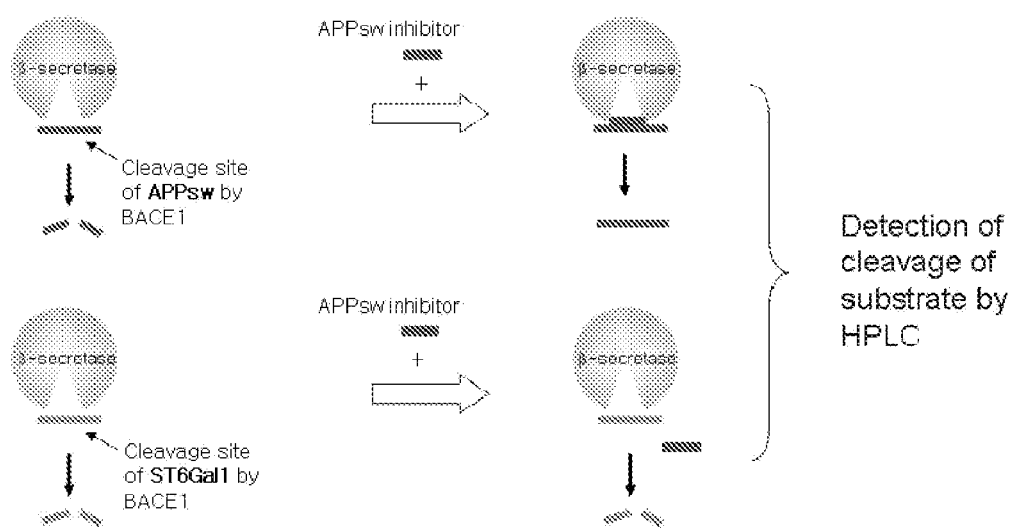
FIG. 16 shows a schematic diagram of specificity assay for APPsw inhibitors.
Figure 17:
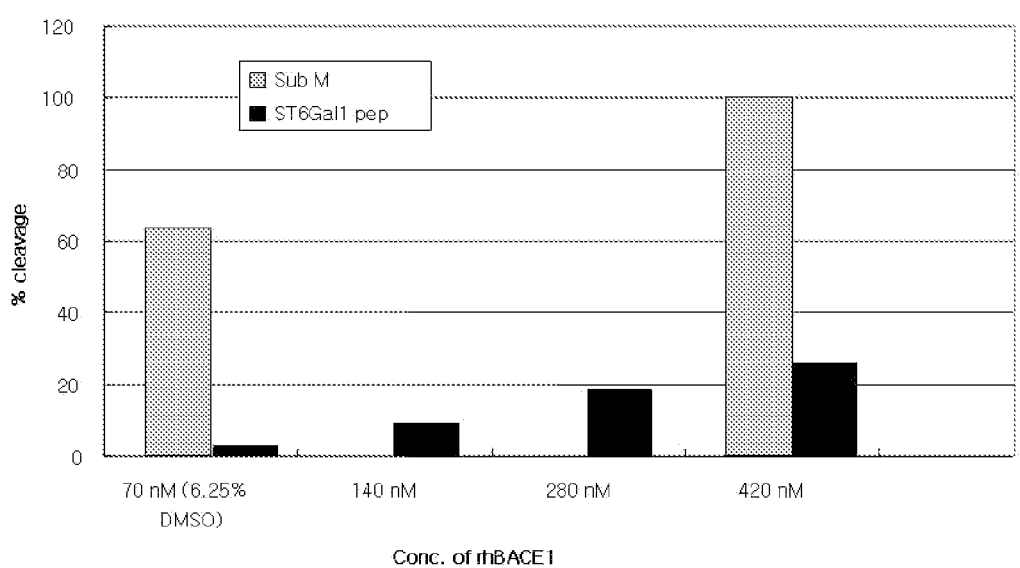
FIG. 17 shows cleavage rate of β-secretase substrates at various β-secretase concentrations.

One of the advantages of the APP inhibitor described in the present invention is that it is a peptide or a mimetic that bind to the β-secretase cleavage site of APP, thus not affecting other β-secretase substrates. To confirm the specificity of the inventive APP inhibitor, two different types of substrates were used, APP Sub M and ST6Gal1. Both substrates are cleaved by β-secretase under normal conditions and the effect of the inventive APP inhibitor on the substrate cleavage was monitored by HPLC (See the schematic diagram in FIG. 16.) To carry out these experiments, the concentration of β-secretase required for cleavage of both substrates was determined as shown in FIG. 17. For substantial cleavage of ST6Gal1 substrate, 420 nM of the enzyme was required. Therefore, 420 nM of β-secretase was used for the following experiment.

Figure 18:
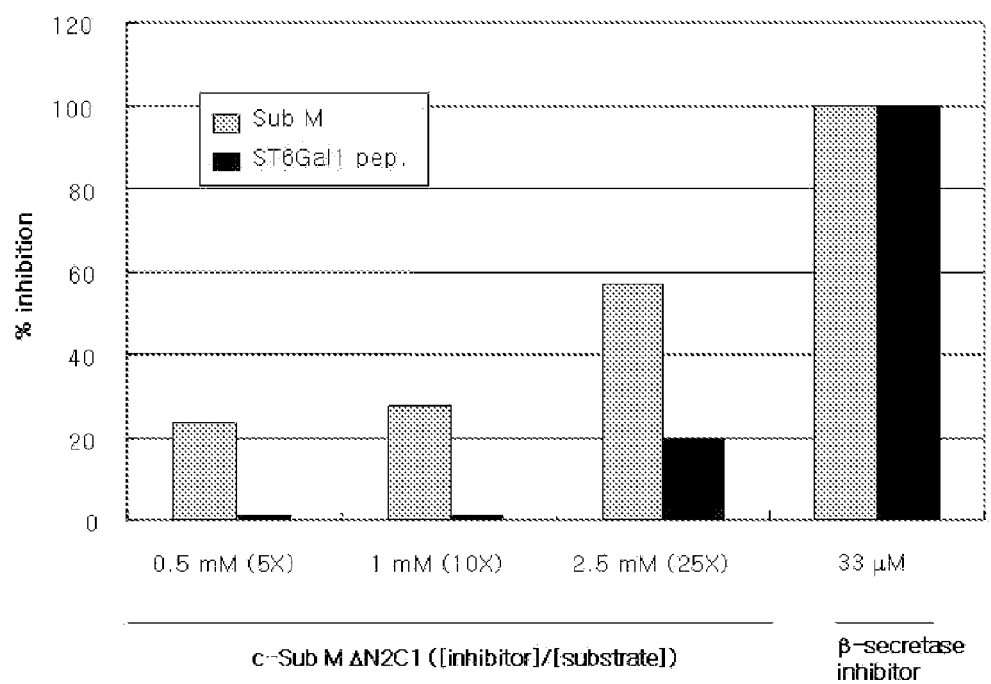
FIG. 18 shows inhibitory activities of APPsw inhibitor on each β-secretase substrate.

Inhibitory activity of inhibitors, APPsw inhibitor, c-Sub MΔN2C1 and commercially available β-secretase inhibitor, on each β-secretase substrate was observed as shown in FIG. 18. When a 25-fold increase in the amount of the inhibitor was added, about 60% of Sub M cleavage was blocked and only 25% of ST6Gal1 peptide cleavage was blocked. However, the commercially available β-secretase inhibitor was equally effective in blocking both substrates. Therefore, the inventive APP inhibitor is specific for APP.

Example 14

Peptides that Bind to the γ-Secretase Cleavage Site of APP

Figure 19:
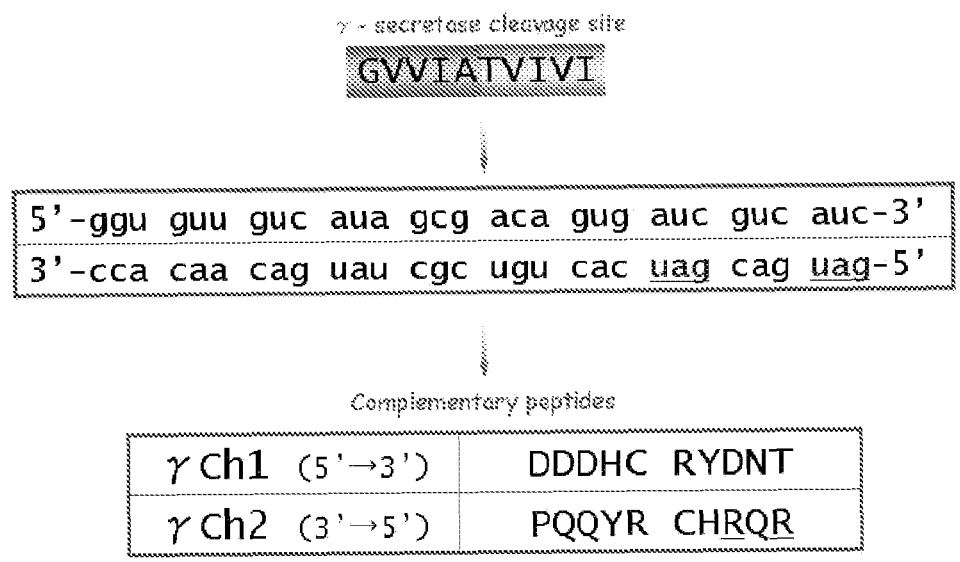
FIG. 19 shows process of obtaining complementary peptides for APP γ-secretase cleavage site. A γ-secretase cleavage site is depicted as GVVIATVIVI (SEQ ID NO:8). The mRNA sequence of the γ-secretase cleavage site is depicted as 5'-ggu guu guc aua gcg aca gug auc guc auc-3' (SEQ ID NO:30), which translates to the polypeptide DDDHCRYDNT (SEQ ID NO:31) (γCh1); and the anti-sense mRNA sequence of the γ-secretase cleavage site is depicted as 3'-cca caa cag uau cgc ugu cac uag cag uag-5' (SEQ ID NO:32), which translates to the polypeptide PQQYRCHRQR (SEQ ID NO:9) (γCh2).

Decamer peptide sequences that contain the cleavage site of APP by γ-secretase were used. The sequence is as follow: GVVIATVIVI (SEQ ID NO:8). γ-secretase cleaves the peptide bond between A and T and releases the following cleavage products: GVVIA (SEQ ID NO:41) and TVIVI (SEQ ID NO:42) (FIG. 19).

As described in Example 1, we designed two peptides based on the hydropathic complementary approach. The anti-sense sequences were deduced from the mRNA sequences corresponding to the above-described decamer substrate peptides. Genetic codes were derived from the antisense RNA by reading the sequences either in 5'→3' or 3'→5' directions. As shown in FIG. 19, the following decamer peptide sequences were obtained: DDDHCRYDNT (γ-Ch1(5'→3'), SEQ ID NO:31) and PQQYRCHRQR (γCh23'→5'), SEQ ID NO:9). These peptides are collectively called γ complementary peptides. For γCh2, since there are two stop codons according to the genetic code, arginine has been inserted for the stop codons.

Example 15

γ-Secretase Activity Assay

Since γ-secretase is composed of four components, cloning of γ-secretase gene is impossible. Therefore, cell extracts were used as γ-secretase source. To obtain the cell extracts, after cell lysis with extraction buffer, the lysate was centrifuged at 10,000×g for 1 minute. Afterward, 2× reaction buffer and fluorogenic substrate was mixed and added to the cell lysate. Then, this mixture was incubated at 37° C. and γ-secretase activity was detected at excitation 335 to 355 nm and emission 495 to 510 nm.

Example 16

γ-Secretase Cleavage Activity

Figure 20:
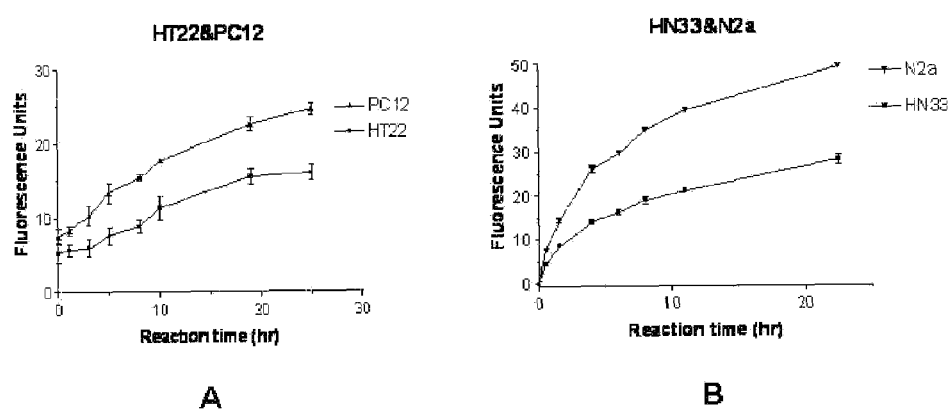
FIGS. 20A and 20B show γ-secretase cleavage activities in several cell lines.

In order to choose a cell line with the highest γ-secretase cleavage activity, four different cell lines were tested according to the assay method described in Example 15. As shown in FIG. 20, all types of cell lines exhibited time dependent γ-secretase activity. Among these, N2a, which is mouse neuroblastoma, showed the highest activity and was chosen as the source of γ-secretase.

Example 17

Figure 21:
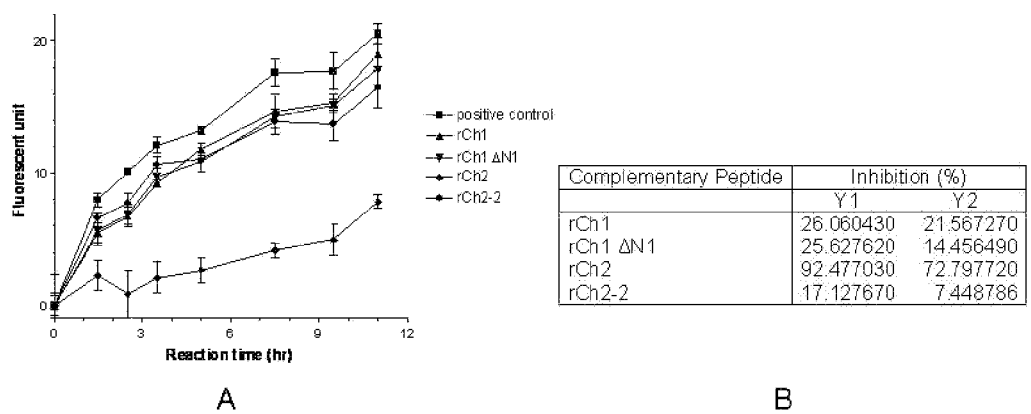
FIGS. 21A and 21B show γ-secretase activities in the presence of complementary peptides. Substrate: 12.5 μM; Complementary peptide: 200 μM; γCh1 (5'→3'): DDDHCRYDNT (SEQ ID NO:31); γCh1 ΔN1: DDHCRYDNT (SEQ ID NO:33); γCh2 (3'→5'): PQQYRCHRQR (SEQ ID NO:9); γCh2-2: PQQYHCHYQ (SEQ ID NO:34). Preincubation period was 1 hr. And γ-secretase (membrane fraction) used was 3 mg/ml.

Effect of Complementary Peptides on γ-Secretase Activity

γ-Secretase activity assay was performed on membrane fractions of N2a cells in the presence of several complementary peptides. After 12.5 μM fluorogenic substrate and 200 μM each of the complementary peptides were preincubated for 1 hour, γ-secretase was added to the mixture. In the course of time, the fluorogenic substrate was cleaved by the γ-secretase. As shown in FIG. 21, rCh2 (3'→5') had the highest inhibitory effect (about 80%) while the other tested complementary peptides inhibited γ-secretase activity only slightly.

Example 18

Cell Based γ-Secretase Assay

In order to test these peptides in the cell for their inhibitory effect on γ-secretase cleavage, a cell based assay was developed. After KEK293 APP cells were cultured in 6 well culture plates with 90% confluency, the cells were treated for 9 hours with N-[N-(3,5-difluorophenacetyl)-L-alanyl]-(S)-phenylglycine t-butyl ester (DAPT) (Dovey H F et al, J. Neurochemistry 2001; 76:173-181), which is a known γ-secretase inhibitor, and complementary peptides. The cells in each well were lysed and these lysates were separated with 15% tris-tricine gel. Western analysis was performed with R1 antibody as primary antibody and goat anti-rabbit-HRP as secondary antibody.

Figure 22:
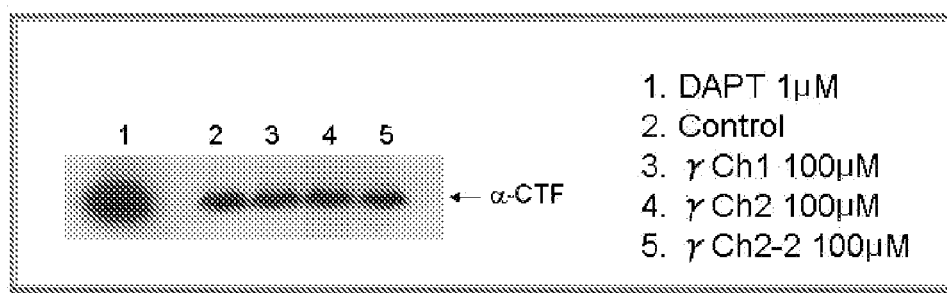
FIG. 22 shows inhibitory effects of the complementary peptides in the cells indicating that the tested peptides are unable to enter the cells across the membrane.
Figure 22:
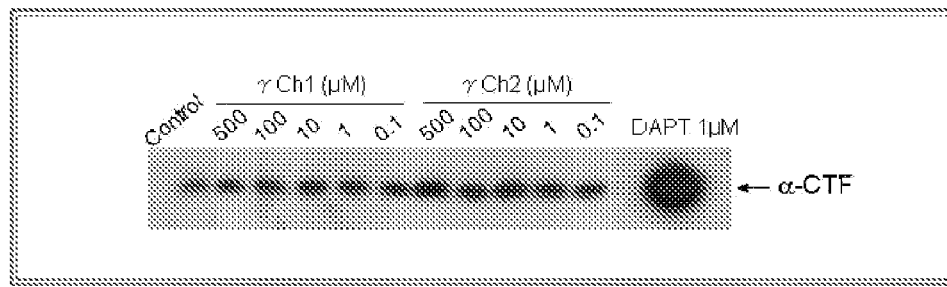

As shown in FIG. 22, DAPT inhibits γ-secretase activity very effectively (lane 1). The resultant α-CTF (C-terminal fragment), which is a product of α-secretase cleavage cannot be cleaved by γ-secretase and instead accumulates in the membrane. However, complementary peptides tested do not have inhibitory effect when compared with control. These results indicate that the complementary peptides cannot be transported into the cell across the membrane. Complementary peptides in the γ-secretase inhibition experiments, γCh2 (3'→5') coupled with polyarginine is tested for translocation across the cell membrane and inhibitory activity in the cells.

Example 19

Alanine Scanning of c-Sub MΔC1N3 (CIQIHF)

Each position of CIQIHF (SEQ ID NO:29) was replaced with Alanine to identify the amino acid that is important for the peptide's inhibitory activity. Replacement with Alanine would presumably reduce the inhibitory activity of the original peptide sequence. The inhibitor activity of the original peptide and the peptides replaced with Alanine at each position were determined as described in Example 4 above. The results show that the amino acids at the first (C), second (I), fourth (I) and sixth (F) positions are significant for the inhibitory activity of CIQIHF.

Example 20

Preparation of App Targeted Inhibitors Designed Based on the HC (Hydropathic Complementarity) Approach 20.1. Peptide Synthesis All the non-labeled and amidated peptides were synthesized with purity better than 95% by A&Pep Co., Inc. (Choong Nam, Korea). All the HC peptides were amidated. The peptides labeled with biotin at N-terminus were synthesized by Peptron, Inc. (Daejeon, Korea). Purity and identity of the peptides were verified by HPLC and mass spectrometry. APP β-Scretase Inhibitor and β-secretase inhibitor IV were purchased from Calbiochem (Darmstadt, Germany). The peptidomimetic, 6-aminohexanoic acid-c-Sub M ΔN3C1 (AHX-c-Sub M ΔN3C1, NH2-(CH2)5-CO—Cys-Ile-Gln-Ile-His-Phe-NH2) was provided by Provid Pharmaceuticals Inc. (NJ, USA). The peptidomimetic, 6-aminohexanoic acid-c-Sub M ΔN3C1 was employed in all the following examples.

20.2. Cell Culture

Human embryonic kidney (HEK) 293 cells stably transformed with the gene for $APP_{695}$ (HEK 293-APP) were used for studies on the inhibitory activity of HC peptides. HEK 293-APP cells were generously supplied by Dr. T W Kim (Columbia University, NY, USA). HEK 293-APP cells were cultured in Dulbecco's Modified Eagle's Medium (DMEM) (Invitrogen, CA, USA) with 10% fetal bovine serum (Hy-Clone, UT, USA) and 300 µg/ml of geneticin (Invitrogen, CA, USA) in a humidified atmosphere of 5% $CO_2$, 95% air at 37° C. Cells were subcultured after trypsinization, and the medium was changed every 2-3 days.

20.3. Binding of BACE1 Substrates to HC Peptides

Reacti-Bind™ maleic anhydride-activated polystyrene plate (Pierce, IL, USA) was coated with 50 µl of HC peptide (200 µM in distilled water) by chemical coupling for 3 h at room temperature (RT) and washed three times with phosphate buffered saline (PBS) containing 0.05% tween 20 (PBST). The plate was blocked with blocking buffer (0.5% gelatin in PBS) for 1 h at RT. After discarding blocking buffer, biotinylated BACE1 substrates (200 µM) in blocking buffer was applied on the plate and incubated for 2.5 h at RT. Each well was washed three times with PBST. The bound biotinylated BACE1 substrates were detected by incubation with streptavidin-horseradish peroxidase (Str-HRP, 125 mU/ml in blocking buffer) for 2 h at RT. Color reaction was carried out with 50 µl of 3,3',5,5'-Tetramethylbenzidine Liquid Substrate (Sigma-Aldrich, MO, USA). After stopping the reaction by addition of an equal volume of 1 N HCl, absorbance at 450 nm was read in an automated ELISA reader (EL 312e, Bio-Tek Instruments, VT, USA). All assays were carried out in duplicate.

20.4. Result

Figure 24:
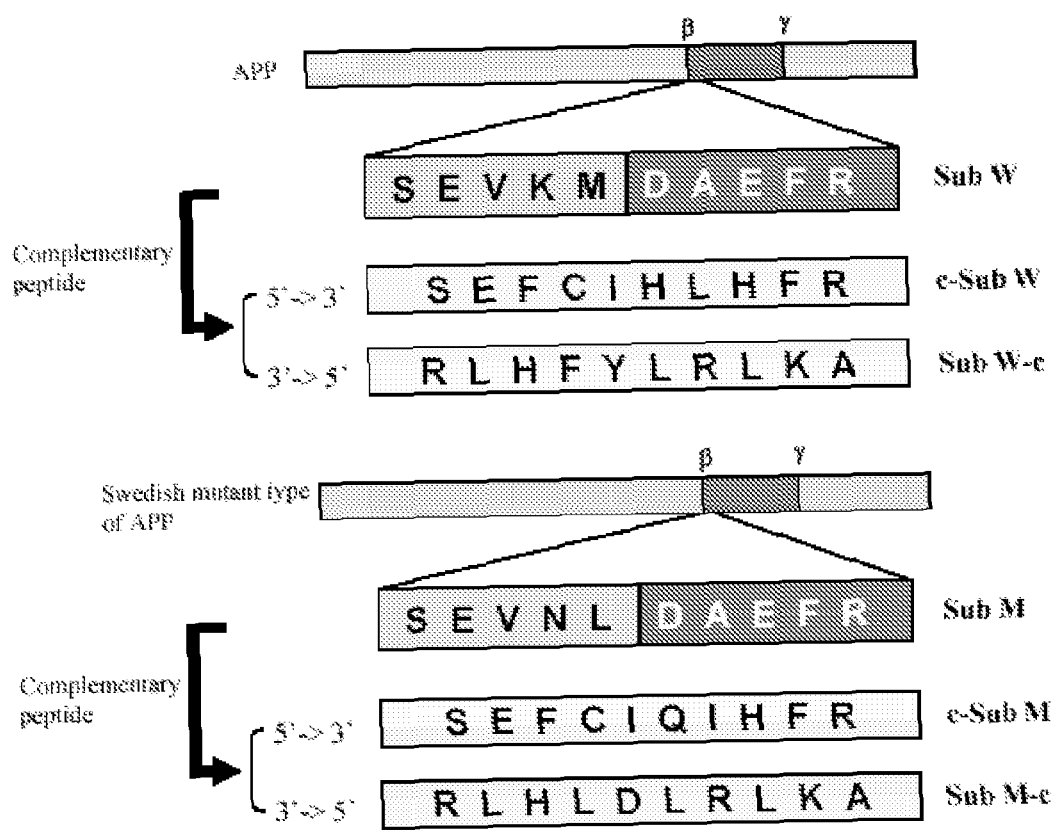
FIG. 24 shows a design of HC peptide using hydropathic complementary (HC) approach. The non-coding strands of DNA sequences corresponding to the 10 amino acids surrounding the μ-cleavage site of wild type and Swedish mutant type of APP were read either in 5'→3' or 3'→5' directions, and codons were predicted. Sub W (SEQ ID NO:1): wild type APP substrate; c-Sub W (SEQ ID NO:6): the HC peptide sequence read from Sub W DNA in 5'→3' direction; Sub W-c (SEQ ID NO:14): the HC peptide sequence read from Sub W DNA in 3'→5' direction; Sub M (SEQ ID NO:2): Swedish mutant APP substrate; c-Sub M (SEQ ID NO:7): the HC peptide sequence read from Sub M DNA in 5'→3' direction; Sub M-c (SEQ ID NO:12): the HC peptide sequence read from Sub M DNA in 3'→5' direction.

The peptide corresponding to the 10 amino acid region containing the β-cleavage site of Swedish mutant type of APP (APPsw) in the center is cleavable by rhBACE1 in vitro. The decapeptide substrate containing a fluorescence group and a quencher on either side of the molecule is commonly used for in vitro assay of BACE1. A molecule that binds to and inhibits cleavage of the decapeptide substrate by BACE1 most likely inhibits cleavage of APP by BACE1 in cells as well, if the molecule enters the cell. Decapeptides that potentially bind to the decapeptide APP substrate for BACE1 by HC approach were designed as shown in FIG. 24.

The decapeptide (SEVNL/DAEFR) corresponding to the β-cleavage site of Swedish mutant type of APP was designated as Sub M (31,32), and the corresponding DNA sequence was used for prediction of HC peptides. The codons read in 5'->3' direction from the non-coding strand was designated as c-Sub M (SEFCIQIHFR) and the peptide sequence read in 3'->5' direction was designated as Sub M-c (RLHLDLRLKA), respectively. The decapeptides corresponding to the β-cleavage site of the wild type of APP was designated as Sub W (SEVKM/DAEFR), and the two HC decapeptide sequences derived from the non-coding strand of Sub W DNA were designated as c-Sub W (SEFCIHLHFR) and Sub W-c (RLHFYLRLKA), respectively (FIG. 24). Even though more than 99% of AD patients have wild type of APP, the wild type substrate is poorly cleaved by BACE1 in vitro. Therefore, most of the enzyme assays was carried out with Sub M.

Example 21

Assay for Inhibitory Activity of HC Peptides Using Fret System In Vitro 21.1. Procedure In this assay system, fluorescence resonance energy transfer (FRET) technology was utilized. Swedish mutant APP substrate (f-Sub M) with a fluorescent donor and a proprietary quenching acceptor (7-methoxycoumarin-4-acetyl-SEVNLDAEFRK(Dnp)-RR-NH2) was purchased from R&D systems, Inc (MN, USA). The donor fluorescence energy is significantly quenched by the acceptor. Upon cleavage of substrate by rhBACE1 (R&D Systems, Inc., MN, USA), the fluorescence donor is separated from the quenching group, restoring the full fluorescence yield of the donor. f-Sub M (10 µM) was pre-incubated with HC peptide in assay buffer (0.1 M NaOAc, pH 4.0) for 2 h at RT. After pre-incubation, substrate and HC peptide mixture in assay buffer was transferred to FluoroNunc™ 96 well white plate (Nunc, Roskilde, Denmark), and rhBACE1 (70 nM) was added. Time-dependent emission of fluorescence (excitation at 320 nm, emission at 405 nm) was monitored in a Molecular Devices SpectraMax Gemini EM fluorescence reader (CA, USA) for 1 h at 37° C. All assays were carried out in duplicate.

21.2. Result—HC Peptides Bound to Sub M and Inhibited its Cleavage.

Figure 25A:
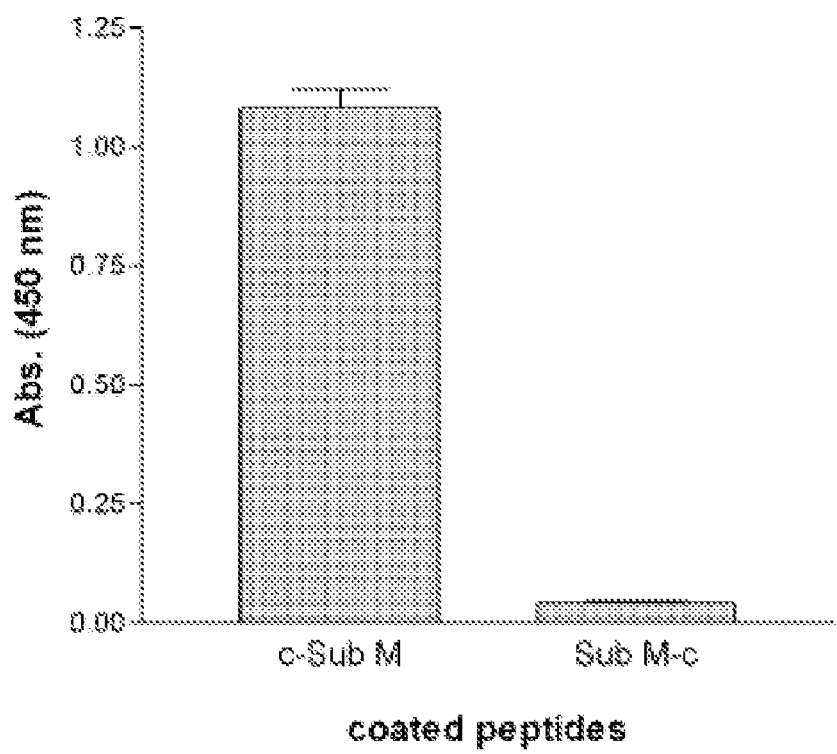
FIGS. 25A and 25B show binding and inhibitory activity of HC peptides for Sub M. 25A shows binding of Sub M to HC peptides. HC peptides were chemically coupled on the wells of a microtiter plate, and biotin labeled Sub M was applied to the HC peptide coated wells. The binding was detected with Str-HRP as described in Experimental Procedures. 25B shows effect of HC peptides on the cleavage of f-Sub M by rhBACE1. HC peptides (1 mM) were preincubated with f-Sub M (10 μM) for 2 h at RT and cleaved with rhBACE1 as described in Experimental Procedures.
Figure 25B:
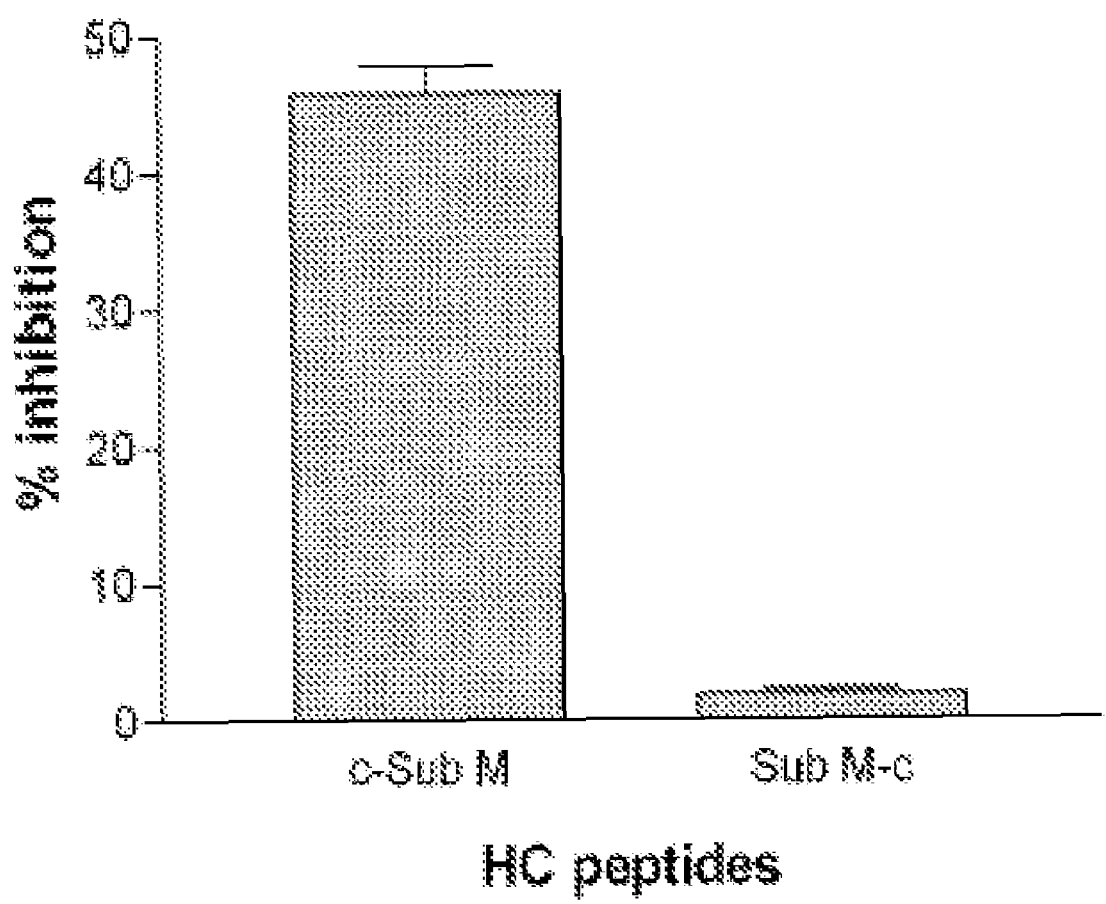

The HC peptides were chemically coupled to the surface of a microtiter plate to minimize the different coating efficiency of peptides, and the Sub M labeled with biotin (bio-Sub M) was applied. bio-Sub M bound to c-Sub but not to Sub M-c (FIG. 25A). To test inhibitory activity of HC peptide, FRET assay system was used as described above. After preincubation with HC peptide, f-Sub M was cleaved with rhBACE1. Consistent with the result of the binding assay, c-Sub M but not Sub M-c inhibited the cleavage of Sub M (about 50% inhibition was obtained at a concentration of c-Sub M that was 100 fold higher than that of substrate. FIG. 25B).

Example 22

Activities of Deletion Types of HC Peptides

The information on core sequence necessary for the inhibitory activity of HC peptides will be useful for design of peptidomimetic compounds. Also, shorter peptides may enter the cells. APP processing is known to occur in endoplasmic reticulum (ER)/Golgi complex and endosome. Therefore, HC peptides have to pass through cell membrane.

Serial deletions were made from either side of c-Sub M, and it was investigated if the deletions had any effect on the binding as well as the cleavage of Sub M as shown in Table 1.

the other hand, deletion of three, four and five amino acids from C-terminus increased the inhibitory activity two folds (greater than 90%) as the deletion of one amino acid from C-terminus. We noted, however, that these three deletion forms aggregated during enzyme assay. Therefore, we decided to focus on c-Sub M ΔC1 for further analysis. Serial deletion of c-Sub M ΔC1 from the N-terminus showed that up to three amino acids (c-Sub M ΔN3C1) can be removed without sacrificing the inhibitory activity too much (Table 2). All deletion forms showed lower binding activity for Sub M than the decapeptides. Nevertheless c-Sub M ΔC1 and one amino acid deletion from N-terminal of c-Sub M ΔC1 showed relatively high binding activity for Sub M (Table 2).

TABLE 1

| Inhibitor Name | Sequence | Binding activity [Abs. (450 nm)] | Inhibitory activity [% inhibition] |
|---|---|---|---|
| Sub W-c | R L H F Y L R L K A | 0.008 | 6.2 |
| c-Sub W | S E F C I H L H F R | 0.124 | 81.1 |
| Sub M-c | R L H L D L R L K A | 0.042 | 1.7 |
| c-Sub-M | S E F C I Q I H F R | 1.083 | 45.8 |
| c-Sub M ΔN1 | E F C I Q I H F R | 0.132 | 90.2 |
| c-Sub M ΔN2 | F C I Q I H F R | 0.096 | 44.0 |
| c-Sub M ΔN3 | C I Q I H F R | 0.073 | 2.4 |
| c-Sub M ΔN4 | I Q I H F R | 0.151 | 1.6 |
| c-Sub M ΔN5 | Q I H F R | 0.14 | 13.8 |
| c-Sub M ΔC1 | S E F C I Q I H F | 0.559 | 99.1 |
| c-Sub M ΔC2 | S E F C I Q I H | 0.12 | 29.9 |
| c-Sub M ΔC3 | S E F C I Q I | 0.252 | 95.5 |
| c-Sub M ΔC4 | S E F C I Q | 0.147 | 98.3 |
| c-Sub M ΔC5 | S E F C I | 0.091 | 92.9 |
| c-Sub M ΔC6 | S E F C | 0.135 | 9.2 |
| c-Sub M ΔC7 | S E F | 0.135 | 15.9 |
| APP β-secretase inhibitor | | ND | 93.2 |

As shown in Table 1, serial deletions were made from either side of c-Sub M. These deletion types of HC peptides were tested for their binding activity for Sub M and inhibitory activity for the cleavage of f-Sub M by rhBACE1 as described above. The concentration of HC peptides and f-Sub M was 1 mM and 10 μM, respectively. All the experimental data for the binding activity as well as for the inhibitory activity were within 7% error range. ND: Not Determined.

When four HC decapeptides were compared, c-Sub M showed highest binding to Sub M and other decapeptides, especially c-Sub W, showed weak but significant binding to Sub M. However, c-Sub W showed higher inhibitory activity toward the cleavage of Sub M by rhBACE1 than c-Sub M. It appears that there is no strict relationship between the degree of binding to the substrate and inhibitory activity of different HC peptides.

Serial deletions were made from the N-terminus of c-Sub M. Deletion of three amino acids abolished the inhibitory activity. Deletion of one amino acid from the C-terminus (c-Sub M ΔC1) increased the inhibitory activity two folds (from 45% to 90%). Deletion of an additional amino acid decreased the inhibitory activity to 44%. Deletion of three amino acids abolished the inhibitory activity completely. On

TABLE 2

| Peptide Name | Peptide Sequence | Binding activity [Abs. (450 nm)] | Inhibitory activity [% inhibiton] |
|---|---|---|---|
| c-Sub M ΔC1 | SEFCIQIHF | 0.532 | 92 |
| c-Sub M ΔN1C1 | EFCIQIHF | 0.425 | 93.5 |
| c-Sub M ΔN2C1 | FCIQIHF | 0.183 | 92.2 |
| c-Sub M ΔN3C1 | CIQIHF | 0.292 | 82.9 |
| c-Sub M ΔN4C1 | IQIHF | 0.155 | 2.2 |
| e-Sub M ΔN5C1 | QIHF | 0.135 | 2.9 |

As shown in Table 2, c-Sub M ΔC1 was deleted further from N-terminus. The binding and inhibitory activities of these peptides were determined as described in Experimental Procedures. The concentration of HC peptides and f-Sub M was 0.5 mM and 10 μM, respectively. All the experimental data for the binding activity as well as for the inhibitory activity were within 5% error range.

The inhibitory activity of N-terminal deletion forms of c-Sub M ΔC1 were compared in more details.

Reversed-phase HPLC was also used to analyze the products of enzyme action in vitro. After 100 μM of Sub M and 2.6 mM of each HC peptide were pre-incubated for 2 h at RT, 140 nM of BACE1 was added to the mixture. The mixture was incubated further for 12 h at RT. The cleavage products were separated on a C18 reversed-phase HPLC column (Grace VyDac, CA, USA) using Hewlett Packard model 1050 HPLC system (CA, USA) (13). The sample, applied to the column equilibrated in 0.1% trifluoroacetic acid (TFA) in double distilled water, was then eluted with a gradient of 0-70% of 0.1% TFA in acetonitrile for 40 min. The elution rate was 1 ml/min. The cleavage products were identified at 215 nm and quantitated by integrating the area under each peak.

Figure 26A:
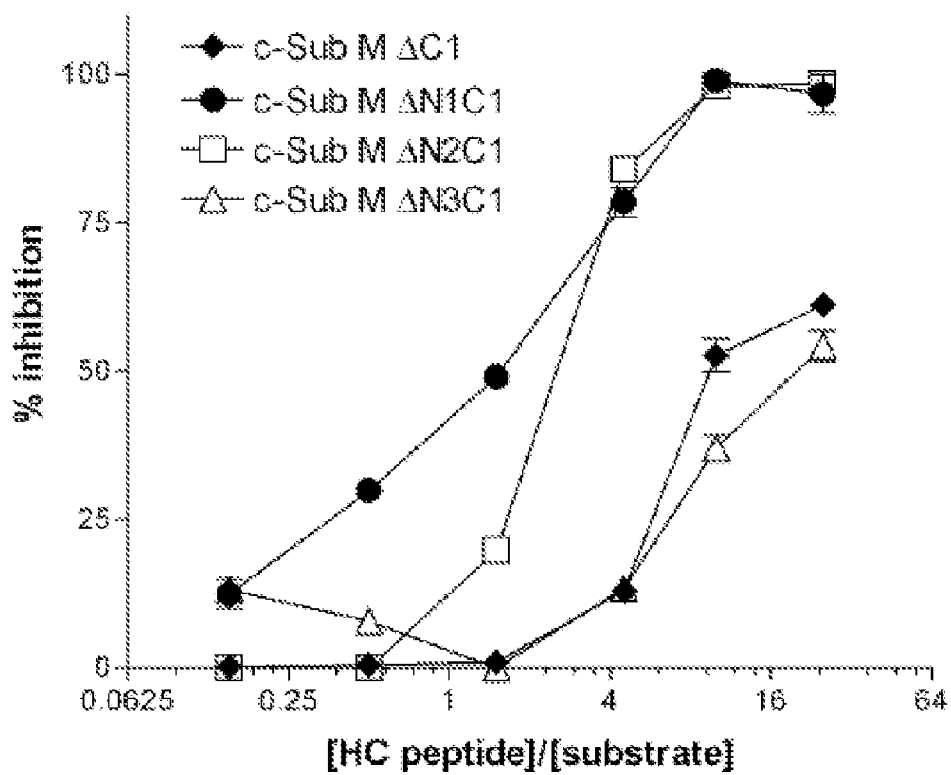
FIGS. 26A and 26B show comparison of inhibitory activity of several deletion types of HC peptides for cleavage of Sub M by rhBACE1. 26A shows inhibitory activity of several HC peptides as determined by FRET assay. The effects of c-Sub M ΔC1, c-Sub M ΔN1C1, c-Sub M ΔN2C1 and c-Sub M ΔN3C1 on the cleavage of f-Sub M by rhBACE1 were compared at different concentrations by FRET assay as described in Experimental Procedures. The concentration of f-Sub M was 10 μM. 26B shows inhibitory activity of several HC peptides as determined by HPLC analysis. Inhibitory activities of c-Sub M ΔN1C1, c-Sub M ΔN2C1 and c-Sub M ΔN3C1 were investigated at higher Sub M concentration (100 μM). Sub M was preincubated with HC peptides for 2 h at RT and cleaved with rhBACE1 for 12 h at RT. The cleaved fragments of Sub M were analyzed by HPLC as described in Experimental Procedures.
Figure 26B:
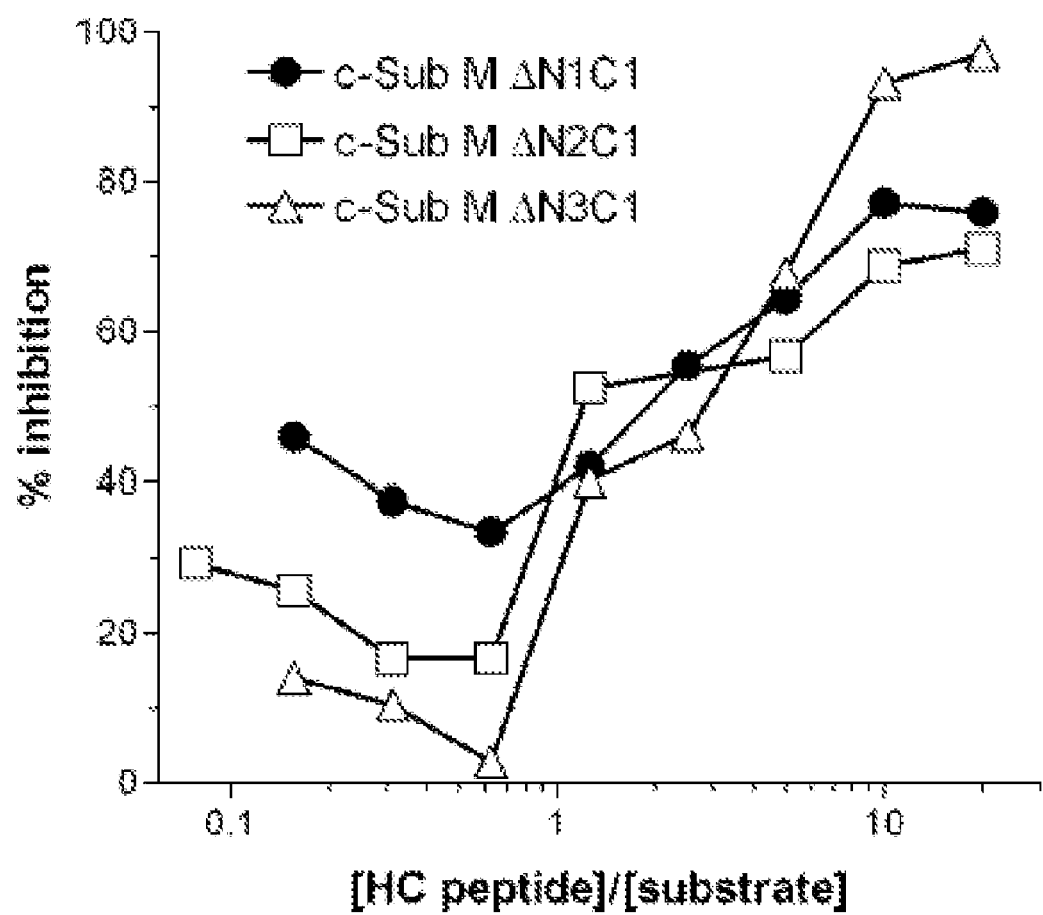

After pre-incubation with HC peptides of different concentrations, f-Sub M (10 μM) was cleaved with rhBACE1. c-Sub ΔN3C1 showed about one tenth of the inhibitory activity of c-Sub M ΔN1C1 (IC50: 15 μM) when the substrate concentration was 10 μM (FIG. 26A). When the substrate concentration was increased ten fold, all three HC peptides showed similar activity (FIG. 26B). In the later experiment, the cleavage of non-labeled Sub M by rhBACE1 was followed by HPLC analysis of the cleavage products. It was not certain if f-Sub M and non-labeled Sub M were cleaved at a similar rate by rhBACE1.

Figure 27:
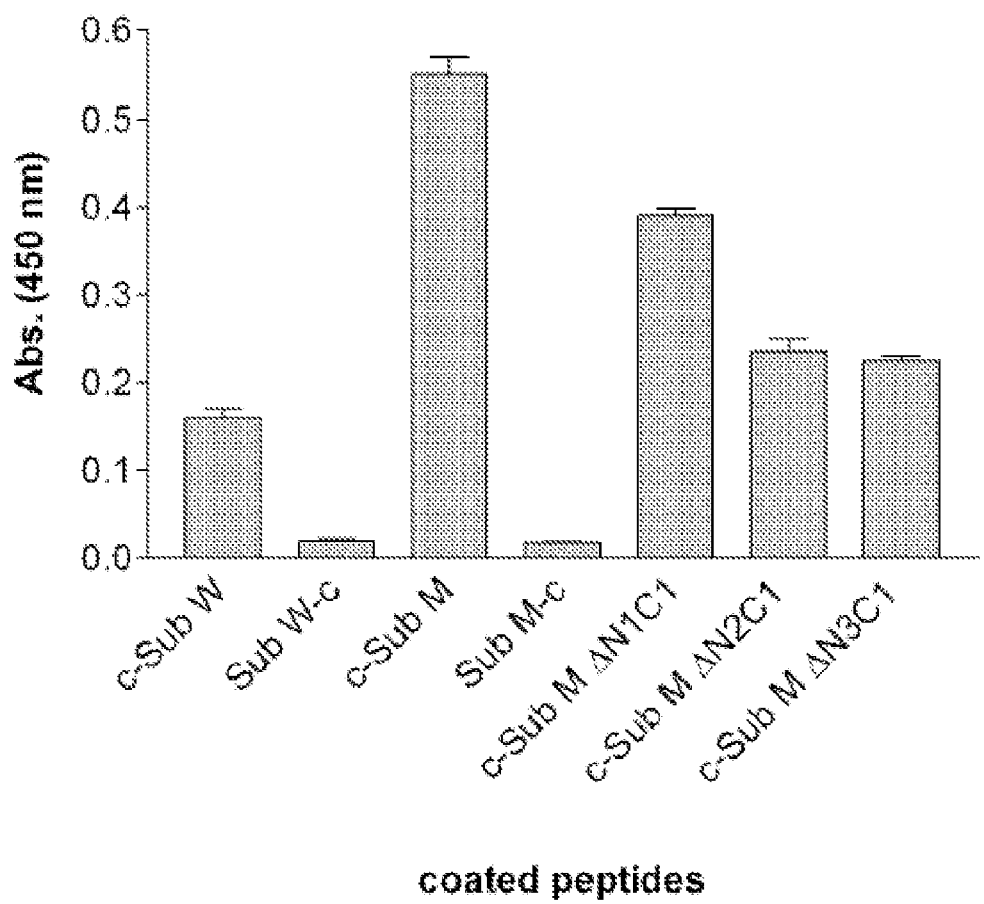
FIG. 27 shows binding between HC peptide and bio-Sub W. HC peptides were chemically coupled on wells of a microtiter plate and biotin labeled Sub W was applied. The binding of bio-Sub W was determined as described in Experimental Procedures.

Thereafter, it was investigated if the c-Sub M and the deletions series bind to wild type Sub W. The results will give us important information on possibility of inhibition of wild type of APP cleavage in cells by the HC peptides derived from Sub M in view of the poor cleavage of Sub W by rhBACE1 in vitro. The results showed that c-Sub M (4 fold) and c-Sub M ΔN1C1 (2.5 fold) bound to Sub W much better than c-Sub W. c-Sub M ΔN2C1 and c-Sub M ΔN3C1 showed similar degree of binding to Sub W as c-Sub W. Sub M-c and Sub W-c showed very low degree (less than 10%) of binding compared to c-Sub W (FIG. 27). Thus, there is possibility that the HC peptides for Sub M (c-Sub M series) or its peptidomimetics will inhibit the cleavage of wild type APP by BACE1 in cells.

Example 23

Assay for Inhibitory Activity of HC Peptide for the Cleavage of Sub M and Sub-ST6Gal1

It was investigated if HC peptide would show specificity for APP in terms of the inhibition of cleavage by BACE1. ST6Gal1 is also cleaved by BACE1. For this experiment, 19 amino acid region (DYEALTL/QAKEFQMPKSQE) that contains the β-cleavage site for investigation was chosen. The 19 amino acid peptide was designated as Sub-ST6Gal1. For investigation of binding of an HC peptide and Sub-ST6Gal1, Sub-ST6Gal1 was labeled with biotin at N-terminus (bio-Sub-ST6Gal1) in the same way as bio-Sub M. c-Sub M ΔN1C1 was chemically coupled on microtiter plate and either bio-Sub M or bio-Sub-ST6Gal1 was applied.

23.1. Procedure

Various concentrations of HC peptide were preincubated with either Sub M (50 μM) or Sub-ST6Gal1 (50 μM, DYEALTLQAKEFQMPKSQE) peptide corresponding to the β-cleavage site of ST6Gal1 for 2 h at RT. The mixtures containing Sub M was treated with 50 nM of rhBACE1 and that containing Sub-ST6Gal1 was treated with 500 nM enzyme for 12 h at RT. Roughly 50% of each BACE1 substrate was cleaved in the absence of HC peptide. The cleavage products were separated on a C18 reversed-phase HPLC column as described above.

23.2. Result—Higher Inhibition of Cleavage of APPSW than ST6Gal1 by BACE1

Figure 28A:
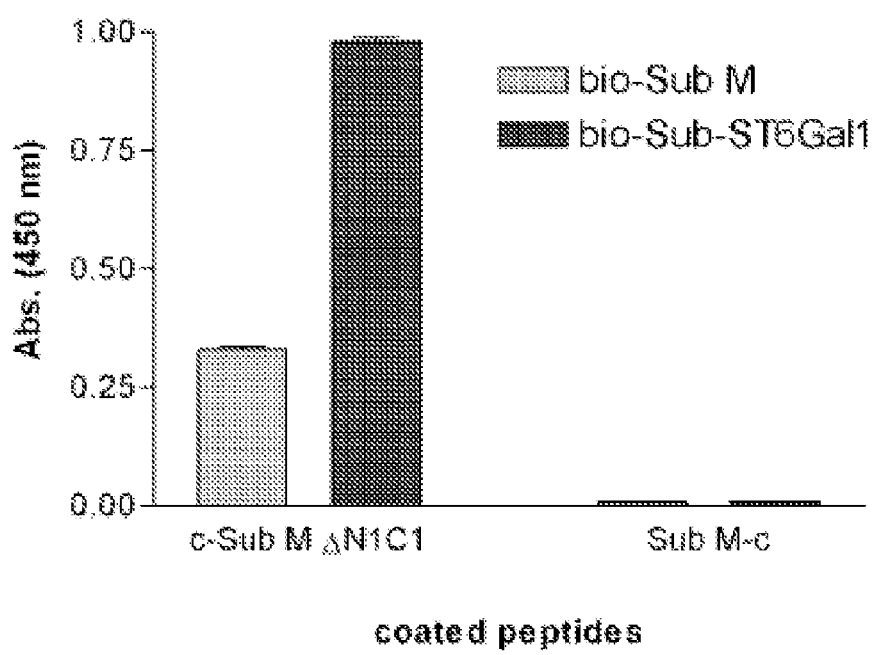
FIGS. 28A and 28B show substrate preference of HC peptide. 28A shows the binding of HC peptides to either Sub M or Sub-ST6Gal1. c-Sub M ΔN1C1 and Sub M-c were chemically coupled on wells of a microtiter plate and either bio-Sub M or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.
Figure 28B:
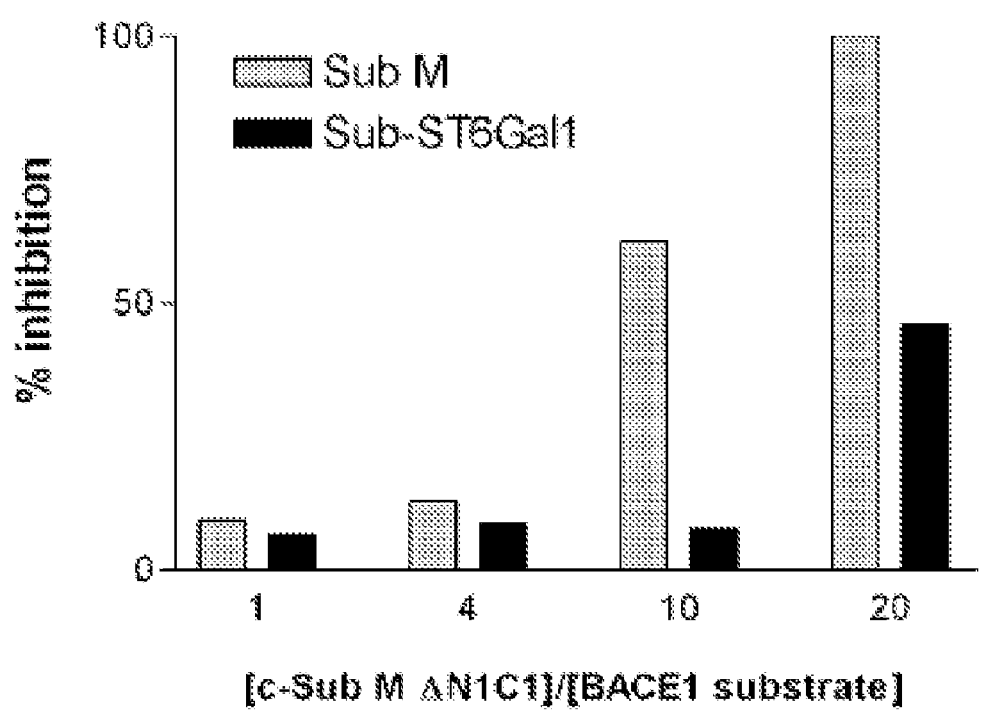

On the contrary to our expectation, the results showed that bio-Sub-ST6Gal1 also bound to c-Sub M ΔN1C1 (FIG. 28A). Thereafter, it was investigated whether c-Sub M ΔN1C1 also inhibits cleavage of Sub-ST6Gal1 by rhBACE1. The results showed that c-Sub M ΔN1C1 also inhibited cleavage of Sub-ST6Gal1 but the peptide was much better inhibitor for the cleavage of Sub M than the cleavage of Sub-ST6Gal (FIG. 28B). For example, at up to 10 inhibitor/substrate ratio, c-Sub M ΔN1C1 showed lower inhibition of the cleavage of Sub-ST6Gal1 by rhBACE1 (about 10%) than the cleavage of Sub M (60% inhibition). At a higher ratio (for example, 20), c-Sub M ΔN1C1 also inhibited the cleavage of Sub-ST6Gal1 (40%) at a lesser extent than the cleavage of Sub M (100%, FIG. 28B).

Example 24

Measurement of Aβ Level

Most of the APP processing including the cleavage by BACE1 occurs in endoplasmic reticulum (ER)/Golgi complex and endosome. It was investigated if c-Sub M and the deletion series would inhibit processing of APP in the cells. For this examination, HEK293 cells transformed with wild type human APP genes for our investigation was chosen.

24.1. Procedure

The culture media from the peptide-treated cells (see above) was harvested and centrifuged at 3500×g for 10 min. Amount of Aβ in the supernatant was determined with human Aβ1-40 immunoassay kits (Signal Select™, BioSource, CA, USA) according to the instruction provided by the company.

24.2. Result—HC Peptides do not Inhibit Synthesis of Aβ in the Cells

It was found that none of the HC peptides inhibited the processing of APP in the cells. This is most likely due to the fact that the peptides can not enter the cells. We found that the c-Sub M ΔN1C1 conjugated with FITC did not enter the cells.

Example 25

Structural Modification of HC Inhibitor

Figure 29A:
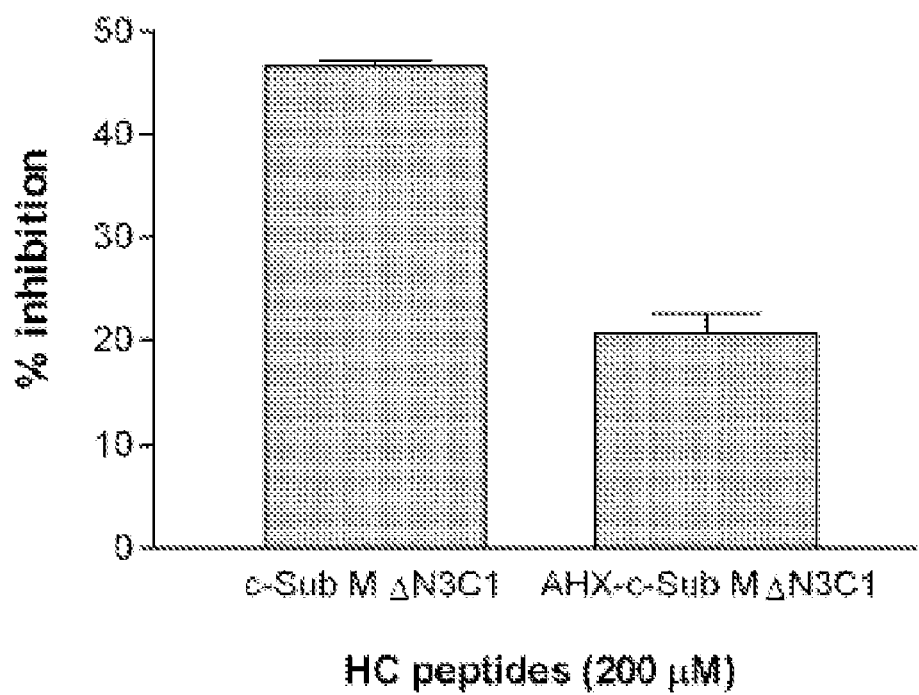

Since HC peptides need to be cell permeable to be active in the cell, chemical modification of an HC peptide was required. c-Sub M ΔN3C1 (CIQIHF) was chosen for chemical modifications. Although this peptide was less active than longer HC peptide, it was the shortest active peptide among the deletion series. To allow an HC peptide pass through cell membrane, addition of lipophilicity would be helpful. For this reason, 6-aminohexanoic acid (AHX) was added to N-terminus of c-Sub M ΔN3C1 (AHX-c-Sub M ΔN3C1, NH2-(CH2)5-CO-Cys-Ile-Gln-Ile-His-Phe-NH2). The addition of AHX to c-Sub M ΔN3C1 reduced in vitro inhibitory activity of non-modified c-Sub M ΔN3C1 by half (FIG. 29A).

Figure 29B:
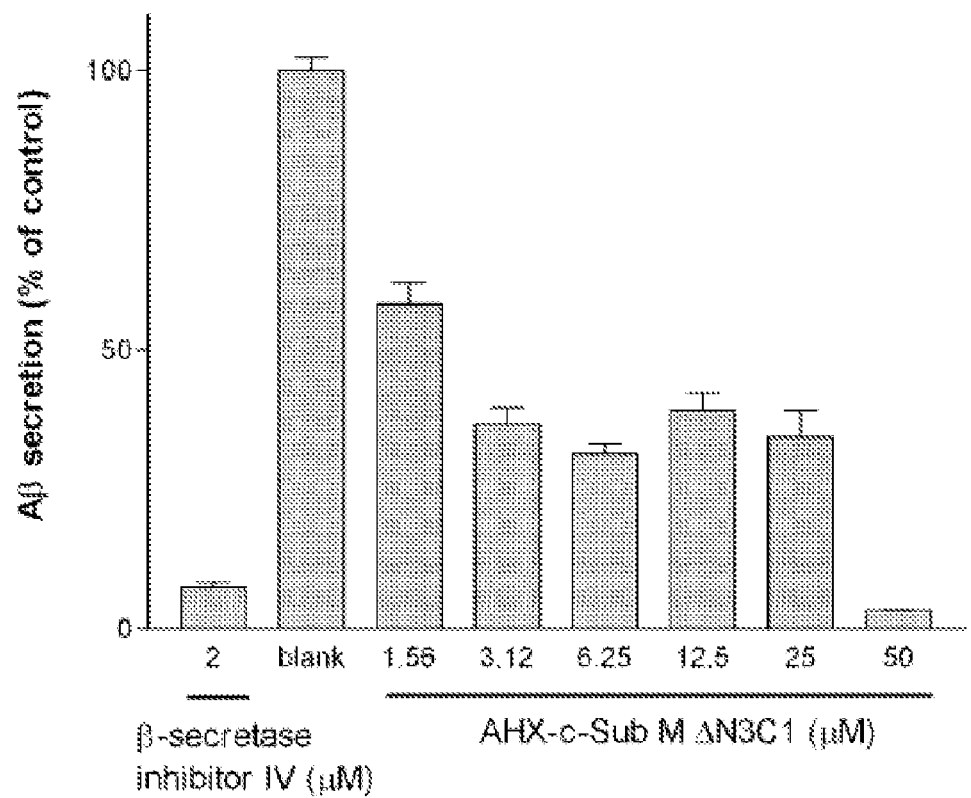
Figure 29C:
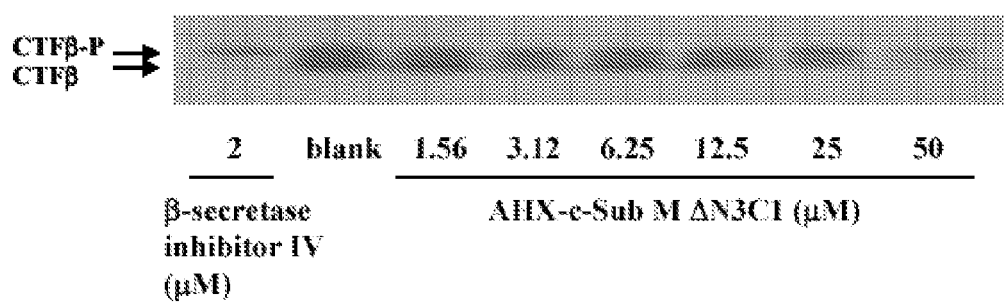
Figure 29D:
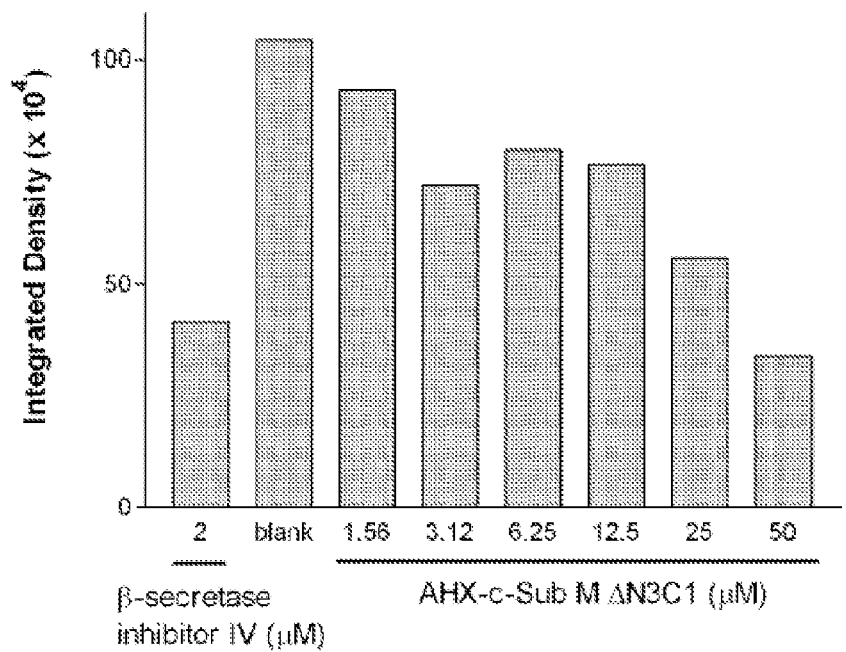

However, AHX-c-Sub M ΔN3C1 inhibited production of Aβ as well as processing of APP in the treated cells. When HEK293-APP cells were treated with increasing concentrations of AHX-c-Sub M ΔN3C1, the amount of Aβ released into the culture medium was reduced in a concentration dependent manner. At 6.25 μM of AHX-c-Sub M ΔN3C1, the amount of Aβ released was reduced by about 70% (FIG. 29B). The production of Aβ was inhibited about 90% by 2 μM of β-secretase inhibitor IV. Both AHX-c-Sub M ΔN3C1 and β-secretase inhibitor IV also inhibited accumulation of the cleavage product CTFβ, the fragment spanning from the β-cleavage site to the C-terminus of APP (FIGS. 29C and 29D). Of interest is that β-secretase inhibitor IV inhibited accumulation of only the nonphosphorylated form of CTFβ. On the other hand, AHX-c-Sub M ΔN3C1 inhibited the accumulation of both forms of CTFβs.

The level of CTFβs was measured as follows:

HEK 293-APP cells were plated on 6 well culture plate (Nunc, Roskilde, Denmark) coated with poly-D-lysine (Sigma-Aldrich, MO, USA). When the confluency of the cells reached 90%, the cells were washed with PBS once, and HC peptide in serum free DMEM was added to the cells. After incubation for 9 h in a humidified CO2 incubator, the cells were lysed in the following solution (10 mM Tris-HCl, pH 7.4, 150 mM NaCl, 1% Triton X-100, 0.25% Nonidet P-40, 2 mM EDTA supplemented with the protease inhibitor mixture (Sigma-Aldrich, MO, USA)) and scraped with a cell scraper. The lysed cells were centrifuged at 12000×g for 10 min at 4° C. The protein in the supernatant was determined by bicinchoninic acid assay (Pierce, IL, USA) [Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) Anal Biochem 150(1), 76-85]. After heating in boiling water, the protein sample (150 µg) in lithium dodecyl sulfate sample buffer (Invitrogen, CA, USA) was loaded on 4-12% bis-tris NuPAGE gel (Invitrogen, CA, USA). After electrophoresis, the proteins in the gel were electrophoretically transferred onto a polyvinylidene difluoride (PVDF) membrane at 100 mA for 80 min. The blotted membrane was fixed with 0.2% glutaraldehyde in PBS for 45 min at RT and treated for 5 min in boiling PBS. CTFβ (the C-terminal fragment of APP generated by BACE1) was detected by treatment of the membrane with 0.5 µg/ml of anti-Aβ N terminal 6E10 antibody (Signetlabs, Inc., MA, USA) followed by incubation with 0.2 µg/ml of anti-mouse antibody coupled with HRP (Amersham Biosciences Ltd. Uppsala, Sweden). The developed film was scanned and the density of CTFβ band was determined by Scion Image Program (Scion Corporation, MD, USA).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

The invention claimed is:

1. A method of specifically inhibiting the β-secretase activity to cleave an amyloid precursor protein (APP), while maintaining its activities to substrates other than APP, said method comprising
   contacting the APP with a compound capable of binding to the β-secretase recognition or cleavage site on the APP,
   allowing the compound to bind to the β-secretase recognition or cleavage site on the APP and
   blocking the β-secretase recognition or cleavage site from binding by the β-secretase, thereby protecting the APP from cleavage by β-secretase,
   wherein the compound is selected from the group consisting of SEFCIHLHFR (SEQ ID NO:6), SEFCIQIHFR (SEQ ID NO:7), EFCIQIHFR (SEQ ID NO:15), FCIQIHFR (SEQ ID NO:16), CIQIHFR (SEQ ID NO:17), IQIHFR (SEQ ID NO:18), QIHFR (SEQ ID NO:19), SEFCIQIHF (SEQ ID NO:20), SEFCIQIH (SEQ ID NO:21), SEFCIQI (SEQ ID NO:22), SEFCIQ (SEQ ID NO:23), SEFCI (SEQ ID NO:24), SEFC (SEQ ID NO:25), FCIQIHF (SEQ ID NO:26), EFCIQIHF (SEQ ID NO:27), CIQI (SEQ ID NO:28), and CIQIHF (SEQ ID NO:29).

2. The method according to claim 1, wherein the β-secretase cleavage site where the compound binds is located within SEVKMDAEFR (SEQ ID NO:1) or SEVNLDAEFR (SEQ ID NO:2) on the amyloid precursor protein.

* * * * *

SEQUENCE LISTING

```
<160> NUMBER OF SEQ ID NOS: 43

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Ser Glu Val Lys Met Asp Ala Glu Phe Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide

<400> SEQUENCE: 2

Ser Glu Val Asn Leu Asp Ala Glu Phe Arg
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Ser Glu Val Lys Met
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 4

Asp Ala Glu Phe Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Ser Glu Val Asn Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Ser Glu Phe Cys Ile His Leu His Phe Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Ser Glu Phe Cys Ile Gln Ile His Phe Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Gly Val Val Ile Ala Thr Val Ile Val Ile
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Pro Gln Gln Tyr Arg Cys His Arg Gln Arg
1               5                   10

<210> SEQ ID NO 10
<211> LENGTH: 30
<212> TYPE: RNA
<213> ORGANISM: Artificial Sequence
<220> FEATURE:
<223> OTHER INFORMATION: Synthetic mRNA
```

-continued

```
<400> SEQUENCE: 10
ucugaaguga aucuggaugc agaauuccga                                          30

<210> SEQ ID NO 11
<211> LENGTH: 30
<212> TYPE: RNA
<213> ORGANISM: Artificial Sequence
<220> FEATURE:
<223> OTHER INFORMATION: Synthetic mRNA

<400> SEQUENCE: 11
agacuucacu uagaccuacg ucuuaaggcu                                          30

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Arg Leu His Leu Asp Leu Arg Leu Lys Ala
1               5                   10

<210> SEQ ID NO 13
<211> LENGTH: 30
<212> TYPE: RNA
<213> ORGANISM: Artificial Sequence
<220> FEATURE:
<223> OTHER INFORMATION: Synthetic mRNA

<400> SEQUENCE: 13
ucugaaguga agauggaugc agaauuccga                                          30

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Arg Leu His Phe Tyr Leu Arg Leu Lys Ala
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Glu Phe Cys Ile Gln Ile His Phe Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Phe Cys Ile Gln Ile His Phe Arg
1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Cys Ile Gln Ile His Phe Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Ile Gln Ile His Phe Arg
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Gln Ile His Phe Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Ser Glu Phe Cys Ile Gln Ile His Phe
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Ser Glu Phe Cys Ile Gln Ile His
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Ser Glu Phe Cys Ile Gln Ile
1               5
```

```
<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Ser Glu Phe Cys Ile Gln
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Ser Glu Phe Cys Ile
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic peptide

<400> SEQUENCE: 25

Ser Glu Phe Cys
1

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Phe Cys Ile Gln Ile His Phe
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic petide

<400> SEQUENCE: 27

Glu Phe Cys Ile Gln Ile His Phe
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Cys Ile Gln Ile
1
```

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Cys Ile Gln Ile His Phe
1               5

<210> SEQ ID NO 30
<211> LENGTH: 30
<212> TYPE: RNA
<213> ORGANISM: Artificial Sequence
<220> FEATURE:
<223> OTHER INFORMATION: Synthetic mRNA

<400> SEQUENCE: 30
gguguuguca uagcgacagu gaucgucauc                                    30

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Asp Asp Asp His Cys Arg Tyr Asp Asn Thr
1               5                   10

<210> SEQ ID NO 32
<211> LENGTH: 30
<212> TYPE: RNA
<213> ORGANISM: Artificial Sequence
<220> FEATURE:
<223> OTHER INFORMATION: Synthetic mRNA

<400> SEQUENCE: 32
ccacaacagu aucgcuguca cuagcaguag                                    30

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Asp Asp His Cys Arg Tyr Asp Asn Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Pro Gln Gln Tyr His Cys His Tyr Gln
1               5

<210> SEQ ID NO 35
<211> LENGTH: 6
<212> TYPE: PRT

```
<213> ORGANISM: Artificial Sequence
<220> FEATURE:
<223> OTHER INFORMATION: Synthetic peptide

<400> SEQUENCE: 35

Ala Ile Gln Ile His Phe
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Cys Ala Gln Ile His Phe
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide

<400> SEQUENCE: 37

Cys Ile Ala Ile His Phe
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Cys Ile Gln Ala His Phe
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

Cys Ile Gln Ile Ala Phe
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Cys Ile Gln Ile His Ala
1               5

<210> SEQ ID NO 41
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 41

Gly Val Val Ile Ala
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide

<400> SEQUENCE: 42

Thr Val Ile Val Ile
1               5

<210> SEQ ID NO 43
<211> LENGTH: 30
<212> TYPE: RNA
<213> ORGANISM: Artificial Sequence
<220> FEATURE:
<223> OTHER INFORMATION: Synthetic mRNA

<400> SEQUENCE: 43
agacuucacu ucuaccuacg ucuuaaggcu                                        30
```